United States Patent
Coutos-Thevenot et al.

(10) Patent No.: US 6,800,794 B1
(45) Date of Patent: *Oct. 5, 2004

(54) NUCLEIC ACID COMPRISING THE SEQUENCE OF A PROMOTER UNDUCTIBLE BY STRESS AND A GENE SEQUENCE CODING FOR A STILBENE SYNTHASE

(75) Inventors: Pierre Coutos-Thevenot, Poitiers (FR); Rüdiger Hain, Langenfeld (DE); Peter-Helmut Schreier, Köln (DE); Michel Boulay, Livry-sur-Seine (FR); Robert Esnault, Gif-sur-Yvette (FR)

(73) Assignees: Champagne Moet & Chandon, Epernay (FR); Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/622,257

(22) PCT Filed: Feb. 12, 1999

(86) PCT No.: PCT/FR99/00316

§ 371 (c)(1), (2), (4) Date: Jan. 2, 2001

(87) PCT Pub. No.: WO99/41392

PCT Pub. Date: Aug. 19, 1999

(30) Foreign Application Priority Data

Feb. 13, 1998 (FR) .............................. 98 01742

(51) Int. Cl.$^7$ .................. C12N 15/09; C12N 15/63; C12N 15/82; A01H 5/00
(52) U.S. Cl. ............ 800/298; 800/278; 536/23.6; 435/419; 435/320.1
(58) Field of Search ................ 800/278, 298, 800/302, 30; 536/23.6, 23.1, 23.2; 435/419, 469, 320.1

(56) References Cited

PUBLICATIONS

Tregear et al., Functional analysis of linket insertions and point mutations in the x–Amy 2/54 GA–regulation promoter, 1995, Plant Molecular Biology, vol. 29, pp. 749–758.* http://www.promega.com/pnotes/44/luehrsen/luehrsen.html; "Firefly Luciferase as a Reporter for Plant Gene Expression Studies"; Kenneth R. Luehrsen, et al., Stanford University.

http://www.cpes.sussex.ac.uk/undergrad/coursenotes/ehh/lec8/8.pdf; "Hosts For Gene Cloning in Plants".

* cited by examiner

Primary Examiner—Amy J. Nelson
Assistant Examiner—Russell Kallis
(74) Attorney, Agent, or Firm—Connolly Bove Lodge & Hutz

(57) ABSTRACT

The invention concerns plants with improved resistance to certain stilbene-sensitive pathogenic agents, and more particularly a set of constructs combining a plant promoter inductible by biotic stress, generated in particular by said pathogens, and gene(s) coding f r a stilbene synthase.

12 Claims, 14 Drawing Sheets

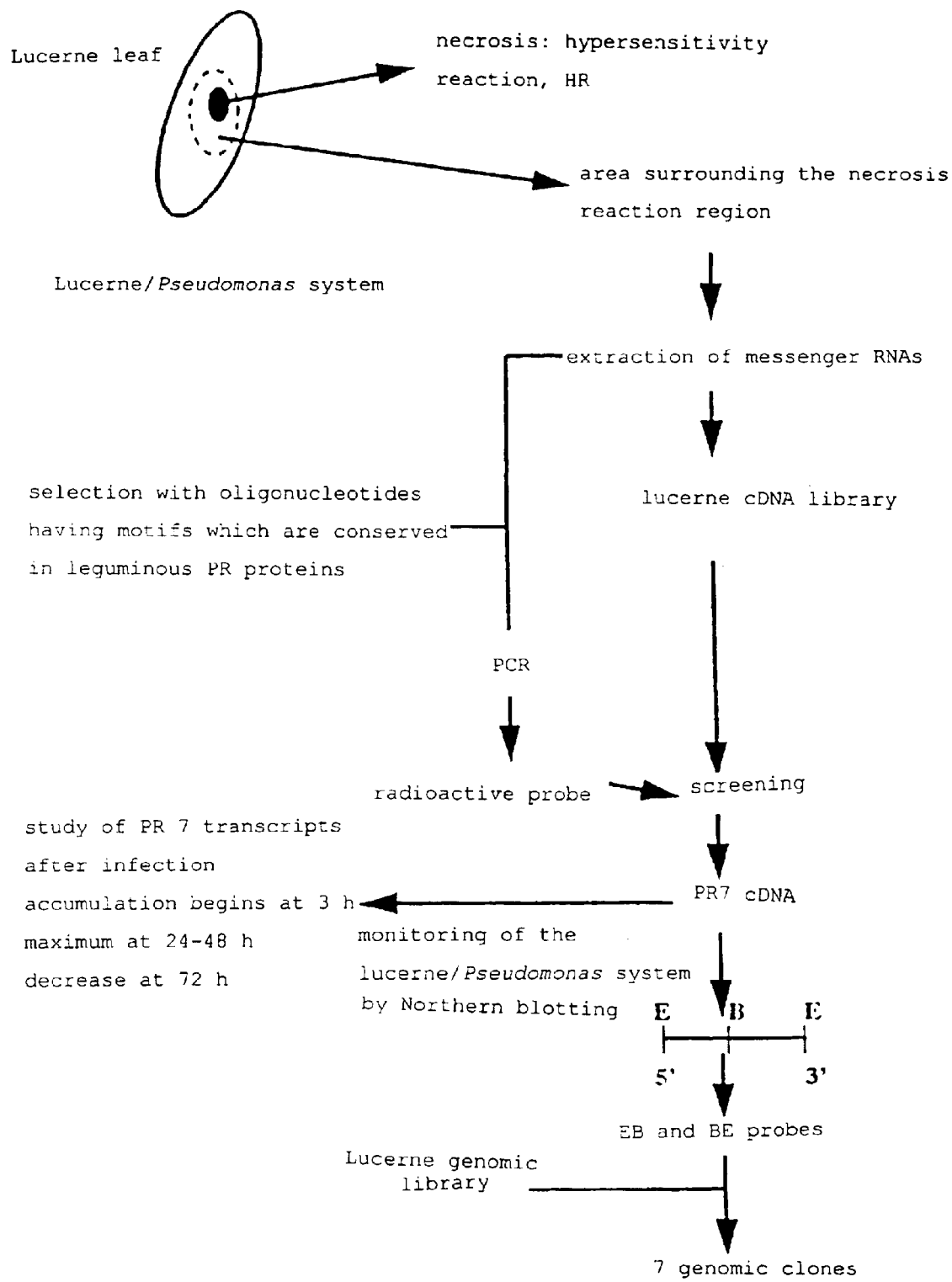

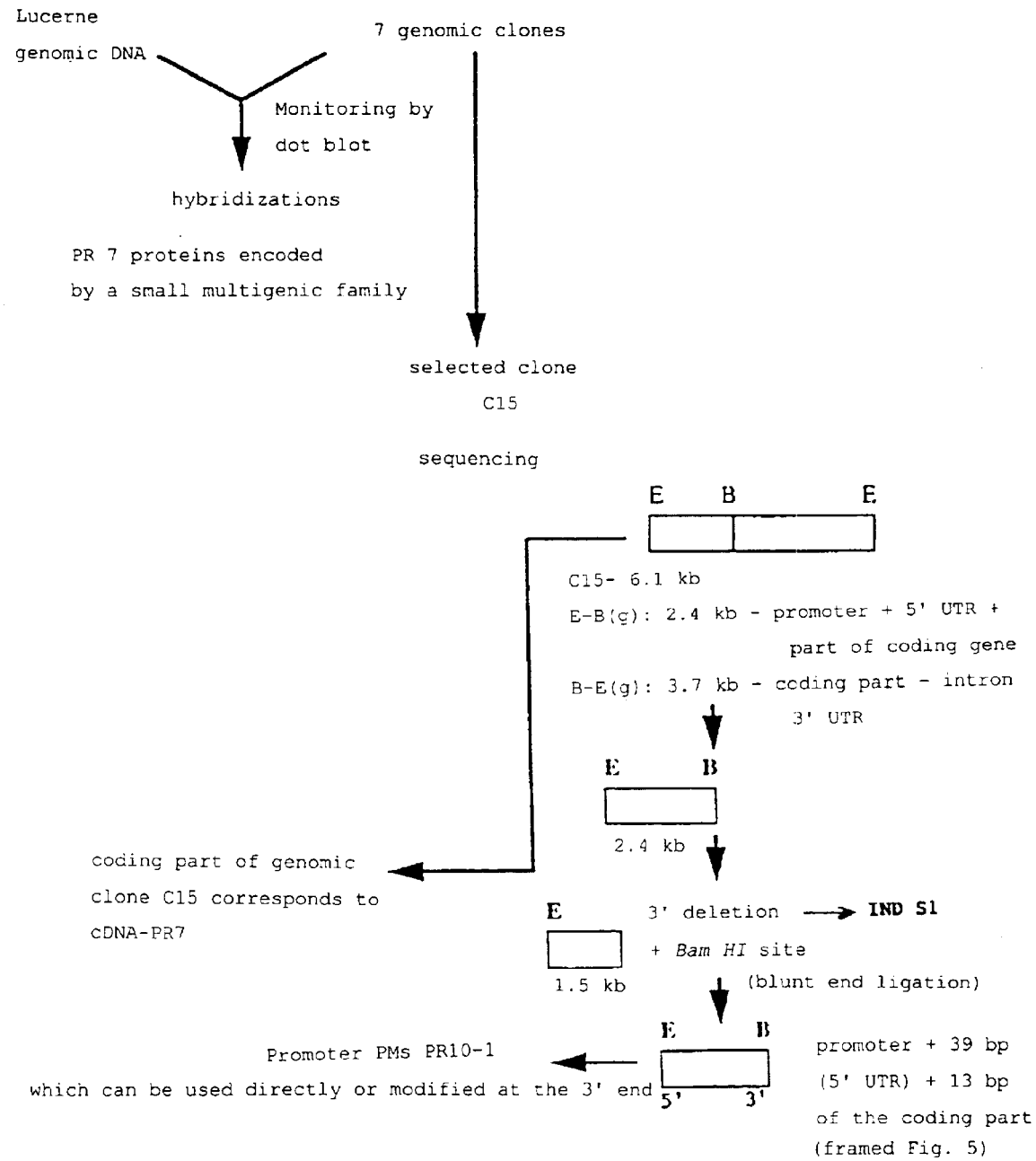

FIGURE 2

| CLONES ISOLATED | SOUTHERN BLOT |
|---|---|
| C3 9.3 — E—B—B—E | 9.6 |
| C12 6.5 — E—B—E | 6.7 (doublet ?) |
| C15 6.1 — E—B—E | |
| C16 5.8 — E—B—E | 5.8 |
| C13 4.8 — E—B—E | 5.2 |
| C8 4.2 — E—BE | 3.5 |
| C7 2.2 — E—BE | 2.4 |
| ( —— = 1kb) | 1.65 (weak signal) |

FIGURE 3

```
gaattcttcaaaaaaaaagttgcccttgagaaactaataagttaataaactaagacctctaa
aaaaaagttaataaactaatatgaatattctctaaacaaaaaataaaactaagaagaatat
attttgcttatttaccagaaaaatactttgcttagtcaaaagaagaagaatattgtgaatta
atttgatactgatgattttttaaagctgtagatatttacgtatttagttaaaaaaatacaatt
attatatatttaattggtgtgtctattcaagtgtttaacttaagttgaggtttattcttatg
ttactaagttggagtggagaagaagactattttgcttgggaggaggaacgcccagtagaatgt
gttattatttttatttttttgtaaggagtagagtgtgttatgttgcttgaataatttttctt
ttgtaggataatgtattagacaaataaattttggaaacacgaccctgtcaaagagtacacggt
aaagggggtggtatacaaaagagtgcgtcgctctattcttcaggtcatttggtttgctacag
tttaggaaattttgggaggaaagaaataacagactgtataacgtcaaagaatgctcggttatt
caggtggtagataagattaagtttcttgcttttgcatgggtgaaggcaaagtttgcttctct
tccattcaattaccatgggtggcggcttagtccgtttaccatactggacataggctaagagt
tttttctttttctcgttttttccattacaagttctttatgtaaatactgttttgacttttggtgtt
cttcccttagtacaccttgtgctaggaaggactattttgatttggtaatatatttcatttta
acctcttaaaaaaaatcaggaaaagaaaaagataaaggtcggaagtgttacctgattataa
aataaatgattaaattgaaaataaagataaataactaaaatgttttctataattaagttaag
agatgaaatatgtaatttttcccaattatatattatgtaagtttttatttatttatatacgt
tgttttgctttgaaatttgagtggtcttggaggagagaaaaacaaaagagaaaagaaaaatt
aatagtagatgcaataattttgttagtccaaataataatatagtttttcttttaaaaataatat
catccaaactcatacattaaaaatattattcaaatttatgtcacgtcacaatgagaaaaaat
ggcccaacgaccttgtattacacatcatcgtcatcatcatctaaagtctaaacaatacatct
tcttttcctataaatacaagactcaactccactcataaatcacacaggcaaacaattaactt
cttaatagtttgttatttcacacattag
```

FIGURE 4

GATCCGGCTTCAATTGAGGAAATTAGAAACGCTCAACGTGCCAAGGGTCCGGCCACCATC
CTAGCCATTGGCACAGCTACTCCCGACCACTGTGTCTACCAGTCTGATTATGCTGATTAC
TATTTCAGAGTCACTAAGAGCGAGCACATGACTGAGTTGAAGAAGAAGTTCAATCGCATA
Tgtaagtatatatattcatgcattaattcttacattcacaacatttctatacatatacga
gtgtgctattaagtgagggtcacctccaagtgaatgaatgtttcaagcttagagaatagc
ttttagctaaattactttaggaaacttgaaaatcattttacatcagtaaccgatattcct
ttcatttgattgtaagggcttgaagagctgttctttgaatcatgtagcattgctagctat
aattaagaataacctttttataatttcttcaatgttaaatgcatgttgatcatcttcaaga
atatactatatgactagtcgttggaaaactaatgtgttcatcttatttcttttacaggGT
GACAAATCAATGATCAAGAAGCGTTACATTCATTTGACCGAAGAAATGCTTGAGGAGCAC
CCAAACATTGGTGCTTATATGGCTCCATCTCTCAACATtACGCCAAGAGATTATCACTGC
TGAGGTACCTAAACTTGGTAAAGAAGCAGCATTGAAGGCTCTTAAAGAATGGGGTCAACC
AAAGTCCAAGATCACCCATtCTTGTATTTTGTACAACCTCCGGTGTAGAAATGCCCGGTG
CAGATTACAAACTCGCTAATCTCTTAGGCCTTGAAACATCGGTTAGAAGGGTGATCTTGT
ACCATCAAGGTTGCTATGCAGGTGGAACTGTCCTTCGAACTGCTAAGGATCTTGCAGAAA
ATAACGCAGGAGCACGAGTTCTTGTGGTGTGCTCTGAGATCACTGTTGTTACATTTCGTG
GGCCTTCCGAAGATGCTTTGGACTCTTTAGTTAGGTCAAGCCCTTTTGGTGATGGGTCA
GCAGCTGTGATTGTTGGATCAGATCCAGATGTCTCCATTGAACGACCCCTCTTCCAACTT
GTTTCAGCAGCACAAACGTTTATTCCTAATTCAGCAGGTGCTATTGCGGGTAACTTACGT
GAGGTGGGACTCACCTTTCACTTGTGGCCTAATGTGCCTACTTTGATTTCCGAGAACATA
GAGAAATGCTTGAATCAGGCTTTTGACCCACTTGGTATTAGCGATTGGAACTCGTTATTT
TGGATTGCTCACCCTGGTGGCCCTGCAATTCTTGATGCAGTTGAAGCAAAACTCAATTTA
GAGAAAAGAAACTTGAAGCAACAAGGCATGTGTTAAGTGAGTATGGTAACATGTCTAGT
GCATGTGTCTTTGTTTATTTTGGATGAGATGAGAAAGAAATCCCTAAAGGGGGAAAAAGC
TATCCACAGGTGACGGATTGGATTGGGGGTACTATTCGGTTTTGGGCCAGGCTTGACCAT
TGAGACCGTTGTGCTGCATAGCGTTCCTATGGTTACAAATTGAgtggaaaacggtaagag
aaatgatatagggacatgtcttattgtattatcagaggaggtgctacgaaagatatgta
catgtatcttcaaagttaataattagtactcctaaatctttattcctatcctaacattg
agggattgtaatttagtgattgttggagggtgcagtcacgtcaggcaagtggatgaaact
gcaagtgcttgtcattctgttatcgggggatcatccatcacactggcggccgctcgagca
tgcat

FIGURE 5

```
gaattcttcaaaaaaaaagttgcccttgagaaactaataagttaataaactaagacctct
aaaaaaaagttaataaactaatatgaatattctctaaacaaaaaataaaactaagaaga
atatattttgcttatttaccagaaaaatactttgcttagtcaaaagaagaagaatattgt
gaattaatttgatactgatgattttttaaagctgtagatatttacgtatttagttaaaaaa
atacaattattatatatttaattggtgtgtctattcaagtgtttaacttaagttgaggtt
tattcttatgttactaagttggagtggagaagaagactattgcttgggaggaggaacgc
ccagtagaatgtgttattatttttttatttttttgtaaggagtagagtgtgttatgttgct
tgaataattttttttttgtaggataatgtattagacaaataaatttggaaacacgaccctg
tcaaagagtacacggtaaaggggtggtatacaaaagagtgcgtcgctctattcttcagg
tcatttggtttgctacagtttaggaaatttgggaggaaagaaataacagactgtataacg
tcaaagaatgctcggttattcaggtggtagataagattaagtttcttgcttttgcatggg
tgaaggcaaagtttgcttctcttccattcaattaccatgggtggcggcttagtccgttta
ccatactggacataggctaagagtttttcttttctcgttttccattacaagttctttat
gtaaatactgttttgactttggtgttcttcccttagtacaccttgtgctaggaaggacta
ttttgatttggtaatatatttcattttaacctcttaaaaaaaatcaggaaaagaaaaag
ataaaggtcggaagtgttacctgattataaaataaatgattaaattgaaaataaagataa
ataactaaaatgttttctataattaagttaagagatgaaatatgtaatttcccaattat
atattatgtaagttttatttattttatatacgttgttttgctttgaaatttgagtggtc
ttggaggagagaaaaacaaaagagaaaagaaaaattaatagtagatgcaataattttgtt
agtccaaataataatatagttttctttaaaaataatatcatccaaactcatacattaaaa
atattattcaaatttatgtcacgtcacaatgagaaaaaatggcccaacgaccttgtatta
cacatcatcgtcatcatcatctaaagtctaaacaatacatcttctttcctataaataca
agactcaactccactcataaatcacacaggcaaacaattaacttcttaatagtttgttat
ttcacacattagggccagATGGAGGATCCGGCTTCAATTGAGGAAATTAGAAACGCTCA
ACGTGCCAAGGGTCCGGCCACCATCCTAGCCATTGGCACAGCTACTCCCGACCACTGTGT
CTACCAGTCTGATTATGCTGATTACTATTTCAGAGTCACTAAGAGCGAGCACATGACTGA
GTTGAAGAAGAAGTTCAATCGCATATgtaagtatatatattcatgcattaattcttacat
tcacaacatttctatacatatacgagtgtgctattaagtgagggtcacctccaagtgaat
gaatgtttcaagcttagagaatagctttagctaaattactttaggaaacttgaaaatca
ttttacatcagtaaccgatattcctttcatttgattgtaagggcttgaagagctgttctt
tgaatcatgtagcattgctagctataattaagaataaccttttataatttcttcaatgtt
aaatgcatgttgatcatcttcaagaatatactatatgactagtcgttggaaaactaatgt
gttcatcttatttcttttacaggGTGACAAATCAATGATCAAGAAGCGTTACATTCATTT
GACCGAAGAAATGCTTGAGGAGCACCCAAACATTGGTGCTTATATGGCTCCATCTCTCAA
CATtACGCCAAGAGATTATCACTGCTGAGGTACCTAAACTTGGTAAAGAAGCAGCATTGA
AGGCTCTTAAAGAATGGGGTCAACCAAAGTCCAAGATCACCCATtCTTGTATTTTGTACA
ACCTCCGGTGTAGAAATGCCCGGTGCAGATTACAAACTCGCTAATCTCTTAGGCCTTGAA
ACATCGGTTAGAAGGGTGATCTTGTACCATCAAGGTTGCTATGCAGGTGGAACTGTCCTT
CGAACTGCTAAGGATCTTGCAGAAAATAACGCAGGAGCACGAGTTCTTGTGGTGCTCT
GAGATCACTGTTGTTACATTTCGTGGGCCTTCCGAAGATGCTTTGGACTCTTTAGTTAGG
TCAAGCCCTTTTTGGTGATGGGTCAGCAGCTGTGATTGTTGGATCAGATCCAGATGTCTC
CATTGAACGACCCCTCTTCCAACTTGTTTCAGCAGCACAAACGTTTATTCCTAATTCAGC
AGGTGCTATTGCGGGTAACTTACGTGAGGTGGGACTCACCTTTCACTTGTGGCCTAATGT
GCCTACTTTGATTTCCGAGAACATAGAGAAATGCTTGAATCAGGCTTTTGACCCACTTGG
TATTAGCGATTGGAACTCGTTATTTTGGATTGCTCACCCTGGTGGCCCTGCAATTCTTGA
TGCAGTTGAAGCAAAACTCAATTTAGAGAAAAAGAAACTTGAAGCAACAAGGCATGTGTT
AAGTGAGTATGGTAACATGTCTAGTGCATGTGTCTTTGTTTATTTTGGATGAGATGAGAA
AGAAATCCCTAAAGGGGGAAAAAGCTAtCCACAGGTGACGGATTGGATTGGGGTACTAT
TCGGTTTTGGGCCAGGCTTGACCATTGAGACCGTTGTGCTGCATAGCGTTCCTATGGTTA
```

FIGURE 5 (continuation 1)

```
CAAATTGAgtggaaaacggtaagagaaatgatatagggggacatgtcttattgtattatca
gaggaggtgctacgaaagatatgtacatgtatcttcaaagttaataattagtactcctaa
atcttttattcctatcctaacattgagggattgtaatttagtgattgttggagggtgcag
tcacgtcaggcaagtggatgaaactgcaagtgcttgtcattctgttatcgggggatcatc
catcacactggcggccgctcgagcatgcat
```

FIGURE 10: Photographic plate 1
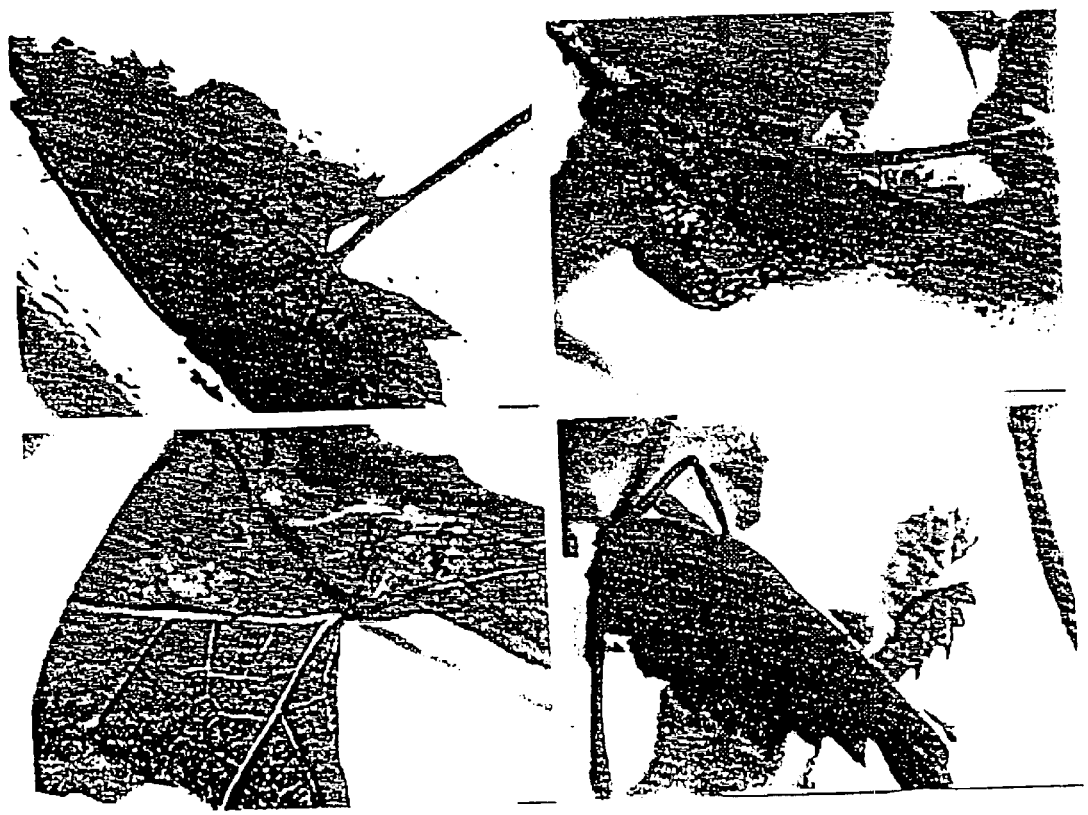

FIGURE 11: Photographic plate 2
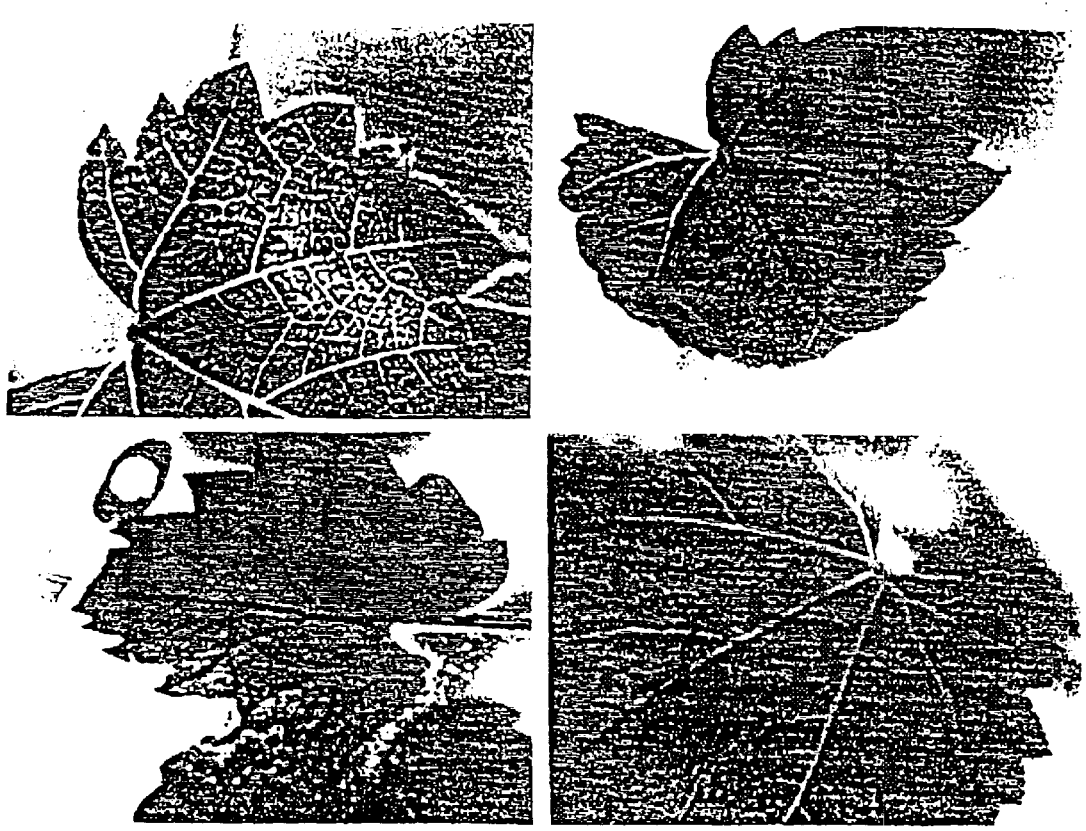

FIGURE 12: Photographic plate 3
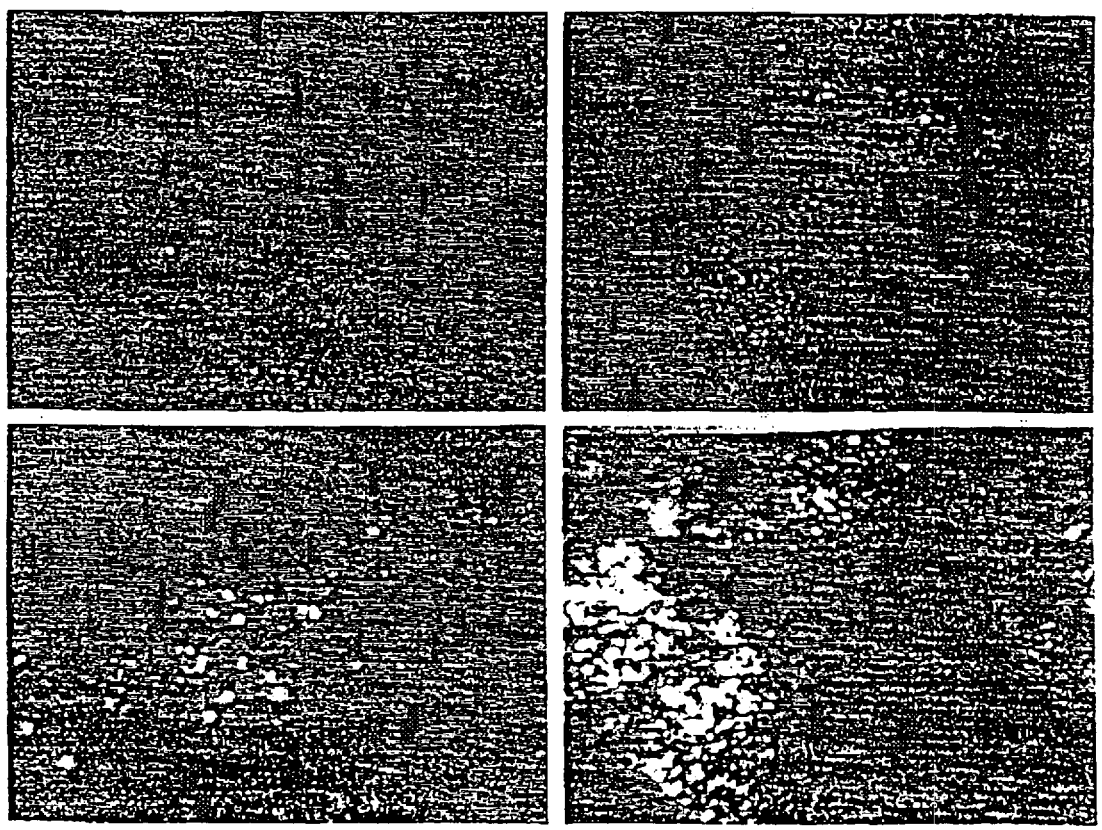

SEQUENCE LISTING

<160> NUMBER OF SEQ ID NOS: 3

<210> SEQ ID NO 1
<211> LENGTH: 1392
<212> TYPE: DNA
<213> ORGANISM: Medigago sativa

<400> SEQUENCE: 1

```
gaattcttca aaaaaaaagt tgcccttgag aaactaataa gttaataaac taagacctct      60
aaaaaaaaag ttaataaact aatatgaata ttctctaaac aaaaaataaa actaagaaga     120
atatattttg cttatttacc agaaaaatac tttgcttagt caaaagaaga agaatattgt     180
gaattaattt gatactgatg attttttaaag ctgtagatat ttacgtattt agttaaaaaa     240
atacaattat tatatattta attggtgtgt ctattcaagt gtttaactta agttgaggtt     300
tattcttatg ttactaagtt ggagtggaga agaagactat ttgcttggga ggaggaacgc     360
ccagtagaat gtgttattat tttttatttt tttgtaagga gtagagtgtg ttatgttgct     420
tgaataattt ttttttgtag gataatgtat tagacaaata aatttggaaa cacgaccctg     480
tcaaagagta cacggtaaag ggggtggtat acaaagagt gcgtcgctct attcttcagg      540
tcatttggtt tgctacagtt taggaaattt gggaggaaag aaataacaga ctgtataacg     600
tcaaagaatg ctcggttatt caggtggtag ataagattaa gtttcttgct tttgcatggg     660
tgaaggcaaa gtttgcttct cttccattca attaccatgg gtggcggctt agtccgttta     720
ccatactgga cataggctaa gagttttcct tttctcgttt ttccattaca agttctttat     780
gtaaatactg ttttgacttt ggtgttcttc cctaagtaca ccttgtgcta ggaaggacta     840
ttttgatttg gtaatatatt tcattttaac ctcttaaaaa aaaatcagga aaagaaaag      900
ataaggtcg gaagtgttac ctgattataa aataaatgat taaattgaaa ataaagataa      960
ataactaaaa tgttttctat aattaagtta agagatgaaa tatgtaatt tcccaattat     1020
atattatgta agtttttatt tatttatat acgttgtttt gctttgaaat ttgagtggtc     1080
ttggaggaga gaaaaacaaa agagaaaaga aaaattaata gtagatgcaa taattttgtt     1140
agtccaaata ataatatagt tttcttaaa aataatatca tccaaactca tacattaaaa     1200
atattattca aatttatgtc acgtcacaat gagaaaaaat ggcccaacga ccttgtatta     1260
cacatcatcg tcatcatcat ctaaagtcta aacaatacat cttcttttcc tataaataca     1320
agactcaact ccactcataa atcacacagg caaacaatta acttcttaat agtttgttat     1380
ttcacacatt ag                                                         1392
```

<210> SEQ ID NO 2
<211> LENGTH: 1805
<212> TYPE: DNA
<213> ORGANISM: Vinifera

<400> SEQUENCE: 2

```
gatccggctt caattgagga aattagaaac gctcaacgtg ccaagggtcc ggccaccatc       60
ctagccattg gcacagctac tcccgaccac tgtgtctacc agtctgatta tgctgattac     120
tatttcagag tcactaagag cgagcacatg actgagttga agaagaagtt caatcgcata     180
tgtaagtata tatattcatg cattaattct tacattcaca acatttctat acatatacga     240
gtgtgctatt aagtgagggt cacctccaag tgaatgaatg tttcaagctt agagaatagc     300
tttttagctaa attactttag gaaacttgaa aatcatttta catcagtaac cgatattcct     360
```

```
ttcatttgat tgtaagggct tgaagagctg ttctttgaat catgtagcat tgctagctat      420
aattaagaat aaccttttat aatttcttca atgttaaatg catgttgatc atcttcaaga      480
atatactata tgactagtcg ttggaaaact aatgtgttca tcttatttct tttacagggt      540
gacaaatcaa tgatcaagaa gcgttacatt catttgaccg aagaaatgct tgaggagcac      600
ccaaacattg gtgcttatat ggctccatct ctcaacatta cgccaagaga ttatcactgc      660
tgaggtacct aaacttggta agaagcagc attgaaggct cttaaagaat ggggtcaacc       720
aaagtccaag atcacccatt cttgtatttt gtacaacctc cggtgtagaa atgcccggtg      780
cagattacaa actcgctaat ctcttaggcc ttgaaacatc ggttagaagg gtgatcttgt      840
accatcaagg ttgctatgca ggtggaactg tccttcgaac tgctaaggat cttgcagaaa      900
ataacgcagg agcacgagtt cttgtggtgt gctctgagat cactgttgtt acatttcgtg      960
ggccttccga agatgctttg gactctttag ttaggtcaag ccctttttgg tgatgggtca      1020
gcagctgtga ttgttggatc agatccagat gtctccattg aacgaccct cttccaactt      1080 gtttcagcag cacaaacgtt tattcctaat tcagcaggtg ctattgcggg taacttacgt      1140
gaggtgggac tcacctttca cttgtggcct aatgtgccta ctttgatttc cgagaacata      1200
gagaaatgct tgaatcaggc ttttgaccca cttggtatta gcgattggaa ctcgttattt      1260
tggattgctc accctggtgg ccctgcaatt cttgatgcag ttgaagcaaa actcaattta      1320
gagaaaaaga aacttgaagc aacaaggcat gtgttaagtg agtatggtaa catgtctagt      1380
gcatgtgtct ttgtttattt tggatgagat gagaaagaaa tccctaaagg gggaaaaagc      1440
tatccacagg tgacggattg gattgggggt actattcggt tttgggccag gcttgaccat      1500
tgagaccgtt gtgctgcata gcgttcctat ggttacaaat tgagtggaaa acggtaagag      1560
aaatgatata ggggacatgt cttattgtat tatcagagga ggtgctacga aagatatgta      1620
catgtatctt caaagttaat aattagtact cctaaatctt ttattcctat cctaacattg      1680
agggattgta atttagtgat tgttggaggg tgcagtcacg tcaggcaagt ggatgaaact      1740
gcaagtgctt gtcattctgt tatcgggga tcatccatca cactggcggc cgctcgagca      1800
tgcat                                                                 1805
```

<210> SEQ ID NO 3
<211> LENGTH: 3209
<212> TYPE: DNA
<213> ORGANISM: Artificial Sequence
<220> FEATURE:
<223> OTHER INFORMATION: DNA sequence comprising the sequence of
      inducible promoter PMs PR10-1 linked to gene for grapevine
      stilbene synthase.
<221> NAME/KEY: promoter
<222> LOCATION: (1)..(3209)
<223> OTHER INFORMATION: Inducible Lucerne promoter linked to grapevine
      stilbene synthase gene

<400> SEQUENCE: 3

```
gaattcttca aaaaaaaagt tgcccttgag aaactaataa gttaataaac taagacctct       60
aaaaaaaaag ttaataaact aatatgaata ttctctaaac aaaaaataaa actaagaaga      120
atatattttg cttatttacc agaaaaatac tttgcttagt caaagaaga agaatattgt       180 gaattaattt gatactgatg attttttaaag ctgtagatat ttacgtattt agttaaaaaa      240
atacaattat tatatatttta attggtgtgt ctattcaagt gttaacttaa agttgaggtt     300
tattcttatg ttactaagtt ggagtggaga agaagactat ttgcttggga ggaggaacgc      360
```

-continued

| | |
|---|---|
| ccagtagaat gtgttattat ttttttatttt tttgtaagga gtagagtgtg ttatgttgct | 420 |
| tgaataattt ttttttgtag gataatgtat tagacaaata aatttggaaa cacgaccctg | 480 |
| tcaaagagta cacggtaaag ggggtggtat acaaaagagt gcgtcgctct attcttcagg | 540 |
| tcatttggtt tgctacagtt taggaaattt gggaggaaag aaataacaga ctgtataacg | 600 |
| tcaaagaatg ctcggttatt caggtggtag ataagattaa gtttcttgct tttgcatggg | 660 |
| tgaaggcaaa gtttgcttct cttccattca attaccatgg gtggcggctt agtccgttta | 720 |
| ccatactgga cataggctaa gagttttttct tttctcgttt ttccattaca agttctttat | 780 |
| gtaaatactg ttttgacttt ggtgttcttc ccttagtaca ccttgtgcta ggaaggacta | 840 |
| ttttgatttg gtaatatatt tcattttaac ctcttaaaaa aaaatcagga aaagaaaaag | 900 |
| ataaaggtcg gaagtgttac ctgattataa aataaatgat taaattgaaa ataaagataa | 960 |
| ataactaaaa tgttttctat aattaagtta agagatgaaa tatgtaattt tcccaattat | 1020 |
| atattatgta agttttttatt tatttttatat acgttgtttt gctttgaaat ttgagtggtc | 1080 |
| ttggaggaga gaaaacaaa agagaaaaga aaattaata gtagatgcaa taattttgtt | 1140 |
| agtccaaata ataatatagt tttctttaaa aataatatca tccaaactca tacattaaaa | 1200 |
| atattattca aatttatgtc acgtcacaat gagaaaaaat ggcccaacga ccttgtatta | 1260 |
| cacatcatcg tcatcatcat ctaaagtcta aacaatacat cttcttttcc tataaataca | 1320 |
| agactcaact ccactcataa atcacacagg caaacaatta acttcttaat agtttgttat | 1380 |
| ttcacacatt agggccagat ggacgatccg gcttcaattg aggaaattag aaacgctcaa | 1440 |
| cgtgccaagg gtccggccac catcctagcc attggcacag ctactcccga ccactgtgtc | 1500 |
| taccagtctg attatgctga ttactatttc agagtcacta agagcgagca catgactgag | 1560 |
| ttgaagaaga agttcaatcg catatgtaag tatatatatt catgcattaa ttcttacatt | 1620 |
| cacaacattt ctatacatat acgagtgtgc tattaagtga gggtcacctc caagtgaatg | 1680 |
| aatgtttcaa gcttagagaa tagcttttag ctaaattact ttaggaaact tgaaaatcat | 1740 |
| tttacatcag taaccgatat tcctttcatt tgattgtaag ggcttgaaga gctgttcttt | 1800 |
| gaatcatgta gcattgctag ctataattaa gaataacctt ttataatttc ttcaatgtta | 1860 |
| aatgcatgtt gatcatcttc aagaatatac tatatgacta gtcgttggaa aactaatgtg | 1920 |
| ttcatcttat ttcttttaca gggtgacaaa tcaatgatca agaagcgtta cattcatttg | 1980 |
| accgaagaaa tgcttgagga gcacccaaac attggtgctt atatggctcc atctctcaac | 2040 |
| attacgccaa gagattatca ctgctgaggt acctaaactt ggtaaagaag cagcattgaa | 2100 |
| ggctcttaaa gaatggggtc aaccaaagtc caagatcacc cattcttgta ttttgtacaa | 2160 |
| cctccggtgt agaaatgccc ggtgcagatt acaaactcgc taatctctta ggccttgaaa | 2220 |
| catcggttag aagggtgatc ttgtaccatc aaggttgcta tgcaggtgga actgtccttc | 2280 |
| gaactgctaa ggatcttgca gaaaataacg caggagcacg agttcttgtg gtgtgctctg | 2340 |
| agatcactgt tgttacattt cgtgggcctt ccgaagatgc tttggactct ttagttaggt | 2400 |
| caagcccttt ttggtgatgg gtcagcagct gtgattgttg gatcagatcc agatgtctcc | 2460 |
| attgaacgac ccctcttcca acttgtttca gcagcacaaa cgtttattcc taattcagca | 2520 |
| ggtgctattg cgggtaactt acgtgaggtg ggactcacct ttcacttgtg gcctaatgtg | 2580 |
| cctactttga tttccgagaa catagagaaa tgcttgaatc aggcttttga cccacttggt | 2640 |
| attagcgatt ggaactcgtt attttggatt gctcaccctg gtggccctgc aattcttgat | 2700 |
| gcagttgaag caaaactcaa tttagagaaa aagaaacttg aagcaacaag gcatgtgtta | 2760 |

-continued

```
agtgagtatg gtaacatgtc tagtgcatgt gtctttgttt attttggatg agatgagaaa    2820
gaaatcccta aaggggggaaa aagctatcca caggtgacgg attggattgg gggtactatt   2880
cggttttggg ccaggcttga ccattgagac cgttgtgctg catagcgttc ctatggttac    2940
aaattgagtg gaaaacggta agagaaatga tataggggac atgtcttatt gtattatcag    3000
aggaggtgct acgaaagata tgtacatgta tcttcaaagt taataattag tactcctaaa    3060
tcttttattc ctatcctaac attgagggat tgtaatttag tgattgttgg agggtgcagt    3120
cacgtcaggc aagtggatga aactgcaagt gcttgtcatt ctgttatcgg gggatcatcc    3180
atcacactgg cggccgctcg agcatgcat                                      3209
```

NUCLEIC ACID COMPRISING THE SEQUENCE OF A PROMOTER UNDUCTIBLE BY STRESS AND A GENE SEQUENCE CODING FOR A STILBENE SYNTHASE

REFERENCE TO RELATED APPLICATION

This Application is a 371 of PCT/FR99/00316, filed Feb. 13, 1998.

BACKGROUND OF THE INVENTION

The present invention relates to plants which exhibit improved resistance to certain pathogenic agents which are sensitive to stilbenes, and relates, more specifically, to a set of constructs which combine a plant promoter which can be induced by a biotic stress, which stress is engendered, in particular, by the said pathogens, with (a) gene(s) encoding a stilbene synthetase.

A large part of the world harvest of cultivated plants is regularly destroyed by parasites and pathogens. Among the possible options for decreasing or preventing the attack by these parasites on cultivated plants, chemical control (plant protection treatments) is the method which is most used. Nevertheless, the application of chemical products is not without consequences for the environment and sometimes presents technological problems as, for example, the appearance of new resistant pathogenic strains or, in the field of oenology, the difficulties which can arise during fermentations (the use of inhibitors of sterol biosynthesis can block yeast growth at the end of fermentation) or the presence of chemical products, such as procymidone, an anti-Botrytis product, which are sometimes found in wine.

The control method which consists in improving the resistance of cultivated plants to the diseases which are caused by these pathogens has been envisaged as a way of overcoming the drawbacks associated with chemical control. It is possible, for example, in a first approach, to achieve this improvement by the sexual route, i.e. using classical genetics, by hybridizing the plants whose resistance is to be improved with tolerant varieties. Nevertheless, this approach is not always feasible (tolerant natural variety not known) or is not permitted by legislation such as, for example, in viticulture as a result of French legislation on Appellations d'Origine Contrôlée (A.O.C.) (registered designations of origin) which limits the grapevine varieties which are to be used for a given appellation (designation).

In a second approach, it is possible, using the modern techniques of cell and molecular biology, to integrate, into the genome of the plant, one or more homologous or heterologous genes which make it possible to overexpress or express a molecule of interest, which is of protein nature, in order to increase the production of a metabolite, or a metabolic pathway, or to open a new biosynthetic pathway or to synthesize a novel molecule for example for increasing the opening of a new biosynthetic pathway, for example increasing the resistance of the plant by reinforcing its defence mechanisms with regard to the pathogens in question.

There are several different defence mechanisms of this type in plants. Some can be regarded as being passive and are linked to the physicochemical characteristics of the cells, the epidermal tissues and/or the organs of the plant. Others belong to the dynamics of gene/gene interactions (plant resistance genes and pathogen avirulence genes, mechanisms of host/pathogen interactions). While these interactions can lead to the development of a hypersensitivity reaction (rapid death of the cells of the plant around the point of infection in order to block colonization of the plant by the microorganism), they can also lead to the synthesis and accumulation of a whole series of compounds. Of these, some can be parietal constituents which are involved in the formation of a "physical" barrier around the point of infection (callose, lignin, hydroxyproline-rich protein: HRGP, etc.), and other compounds can be molecules having antimicrobial functions which are more or less well defined (phytoalexins, pathogen-associated proteins: PR proteins (pathogenesis-related proteins), etc.). The molecules of the phytoalexin type which are synthesized and accumulated by plants during, for example, host/pathogen interactions include, in particular the stilbenes, which are toxic, in particular for microorganisms. The term stilbene designates a group of chemical substances which possess the trans-diphenyl-1,2-ethylene skeleton as the common basal structure, with resveratrol and pinosylvine being among the simplest. This basal skeleton is synthesized in plants by a stilbene synthetase or related enzymes from substrates such as malonyl-CoA, cinnamoyl-CoA or coumaroyl-Coa, which are substances which are present in all plants (flavonoid precursors). Genes for stilbene synthetase or related enzymes have been isolated, sequenced and cloned, in particular from groundnut, orchid and grapevine. Using these genes, it has been possible to transform plants such as potato, lucerne or tobacco, with these plants then exhibiting greater resistance than untransformed plants to pathogen attack (EP-309862; EP-648839; MELCHIOR, F. et al., Arch. Biochem. Biophys. 1991, 288, 2, 552–557; WIESE, W. et al., Plant Mol. Biol. 1994, 26,2,667–677; HAIN, R. et al., Nature 1993, 361, 153–156).

The expression or overexpression of these molecules having antimicrobial functions can provide plants with a "natural" resistance in response to stresses, in particular stresses of the microbial type. However, constitutive overexpression of this type of protein necessarily has disadvantages for the plant (energy cost, slowing down of growth, etc.) (FISCHER, R. et al., The Plant Journal 1997, 11, 3, 489–498).

On the other hand, in some plants, such as grapevine or herbaceous plants, stilbenes are only found in some healthy tissues and at very low concentrations. Conversely following an infection or a lesion, these stilbenes increase strongly at the infected or damaged site, since the stilbene synthetase genes are inducible under conditions of biotic or abiotic stress (for example wounds, ultraviolet rays, etc.).

Nevertheless, this regulation is rarely present in plants of agricultural interest or, when it is present, it can be insufficiently effective. For example, studies on phytoalexin synthesis in the grapevine have demonstrated that the only healthy tissue in which stilbenes, including resveratrol, are present is healthy wood tissue. Stilbene is found to be present in the tissues of the grape berry when, on the one hand, the berry has been subjected to a stress such as attack by a pathogen (*Botrytis cinerea* for grey mould or *Plasmopora viticola* for grape downy mildew) and, on the other hand, only during the period up to the incipient ripening of the young fruit. By contrast, the concentration of the stilbene decreases strongly from incipient ripening to maturation. However, damage due, for example, to Botrytis is rarely encountered during the period up to incipient ripening but rather during the period close to maturation of the berry. For this reason, expression of the stilbene synthetase gene has to be controlled with strong promoters which escape the natural regulation of the gene and which should be inducible, in particular by the stress itself. The present invention specifically relates to a promoter of this nature.

BRIEF SUMMARY OF THE INVENTION

The present invention relates to nucleic acids which comprise the sequence of the promoter for a lucerne PR protein linked to at least one sequence of a gene encoding a stilbene synthetase.

The invention relates, in particular, to nucleic acids according to the invention, characterized in that the promoter for a lucerne PR protein is a promoter which can be induced in plants, in a tissue-specific manner or not, by a biotic or abiotic stress.

The invention also relates to nucleic acids according to the invention, characterized in that the sequence of the promoter for a lucerne PR protein is selected from the group comprising:

a) the IND S1 sequence,
b) any sequence corresponding to a fragment of the IND S1 sequence and having a promoter sequence effect in plants.

The sequences of the promoter for a lucerne PR protein are preferred which exhibit at least 80% homology with the IND S1 sequence. Those sequences are particularly preferred which exhibit at least 90% or 95% homology with the said sequence.

The sequences of promoters for lucerne PR proteins according to the invention were obtained from regulatory sequences of genes for PR proteins by taking advantage of the incompatibility response (hypersensitivity reaction, HR) obtained in the host/parasite relationship between lucerne (*Medicago sativa*) and *Pseudomonas syringae* pv pisi for the purpose of isolating the regulatory sequences of genes which are responsible for this reaction.

When Pseudomonas attacks lucerne, the occurrence of a plant reaction is observed in the region adjacent to the necrosis caused by the bacterial infection.

Plant material was therefore removed following the bacterial attack in order to construct a cDNA library from the messenger RNAs which were produced in the regions adjacent to the necrosis. Amplification by polymerase chain reaction (PCR), using synthetic polynucleotides corresponding to motifs which are conserved in leguminous PR protein genes, enabled a radioactive probe to be obtained which was then used to select transcripts in the cDNA library. One of these (cDNA-PR7) was adopted since, after sequencing, it exhibited good homology with equivalent genes encoding PR proteins and known from other plants (cf. FIGS. 1 and 1a, depicting the general scheme of the method for isolating the promoter).

Analysis showed that it corresponded to a gene encoding a class 10 PR protein according to the VAN LOON (1994) classification. This gene was therefore designated Ms PR10-1 (*Medicago sativa* PR class 10 protein, clone 1). The isolated and cloned cDNA PR7 made it possible to obtain two probes due to the presence of an internal BamHI site (B in FIG. 1). These probes, EB and BE (E corresponding to the EcoRI site in FIG. 1) named respectively 5' and 3', were used to screen a lucerne genomic library. Among the clones obtained which were recognised by the 5' and 3' probes, one of them, C15, was selected and sequenced (6.1 Kb). It itself also possesses, logically, a BamHI site which made it possible to obtain two novel EB and BE fragments of 2.4 kb and 3.7 kb, named respectively E-B(g) and B-E(g), g indicating the genomic nature of the fragments obtained (see FIG. 1a). Fragment E-B(g), which is located in 5' of the C15 clone, and which comprises the promoter and a portion of its Ms PR10-1 gene coding sequence, was inserted into the EcoRI and BamHI sites of the bluescript plasmid. The plasmid was linearized by means of a PstI site which is located upstream of BamHI in fragment E-B(g). A deletion from 3' to 5' was carried n out on this fragment until the IND S1 promoter sequence was obtained (FIG. 3). A blunt end ligation made it possible to reposition another BamHI site, internal to the C15 clone, at the end of the promoter sequence of the Ms PR10-1 gene. Under these conditions, 13 nucleotides of the coding sequence of the Ms PR10-1 gene, located upstream of this BamHI site which is internal to the C15 clone, were thus integrated into the IND S1 promoter sequence: the whole can be isolated with an EcoRI/BamHI digestion (see Example 1).

In the description, PMs PR 10-1 is also intended to mean any nucleic acid fragment of the IND S1 sequence with a promoter effect in plants and the IND S1 sequence with 13 nucleotides of the coding sequence of the Ms PR10-1 gene as described below.

The invention also relates to nucleic acids according to the invention, characterized in that the sequence of a gene encoding a stilbene synthetase, whether homologous or heterologous, is selected from the genes isolated from groundnut, orchid, grapevine and pine genomes (EP-309 862, EP-464 461).

Of the said nucleic acids, preference is given to the nucleic acids which encode a grapevine stilbene synthetase, in particular those described in the article by HAIN, R. et al., Natrue 1993. 361, 153–156 and in that by WIESE, W. et al., Plant Mol. Biol., 1994, 26, 2, 667–677; the nucleic acid corresponding to the sequence vst1 of the said articles is that which is most preferred.

The nucleic acids enabling the stilbene synthetase gene(s) to be expressed will naturally be able to include, in particular, apart from the said gene(s), polyadenylation sequences at the 3' end of the coding strand and enhancer sequences from the said gene or from a different gene.

Naturally, the nucleic acid sequences will have to be adapted in order to ensure that the gene is actually read in the correct reading frame with the promoter and it will obviously be possible to foresee using, if necessary, several promoters of the same type as well as several enhancer sequences.

It is also possible to use the nucleic acids according to the present invention to express several stilbene synthetase genes, either arranged in tandem or carried by different expression systems.

The nucleic acids according to the invention can be used to create expression systems in plants, which systems can be inducible and/or constitutive depending on the tissues or organs of the plant which are transformed (cf. Examples 2, 3 and 4).

The present invention therefore also relates to systems for expressing at least one stilbene synthetase gene in plants, characterized in that they comprise at least one nucleic acid according to the invention. Of the systems according to the invention, preference is given to transformation vectors, particularly transformation vectors of the plasmid type.

Advantageously, the said transformation vectors are characterized in that they can be transferred into Agrobacterium strains.

The stilbene synthetase genes which are able to be expressed by the nucleic acids according to the present invention are placed under the control of the PMs PR10-1 promoter for the purpose of activating, in plants, mechanisms of resistance to pathogens which are sensitive to stilbenes, in particular to resveratrol, to pinosyl grapevine or to their glycosylated derivatives such as picein or to oligomers such as the viniferins. Parasites of this nature which are sensitive to stilbenes and which may be mentioned are *Botrytis cinerea, Plasmopora viticola, Eutypa lata*, etc.

Preference is given to those expression systems according to the invention which are characterized in that they can be induced in plants by a biotic or abiotic stress.

From the said biotic stresses according to the a invention preference is given in particular to biotic stresses which are engendered by the attack of a parasite which is sensitive to stilbenes, such as a virus, a bacterium, a yeast, a fungus, in particular *Botrytis cinerea* or *Plasmopora viticola*.

From the said abiotic stresses according to the invention, preference is given in particular to abiotic stresses engendered by a mechanical wound such as that caused in particular by an insect or by a physical phenomenon such as wind or frost.

The present invention also relates to plant cells which are transformed with a system or a vector according to the invention. Advantageously, the said plant cells are grapevine cells.

The present invention also relates to processes for transforming plant cells using a microbiological method, including the systems or vectors according to the present invention.

The invention furthermore relates to processes for obtaining plants which express one (or several) stilbene synthetase gene(s), characterized in that cells of the said plants are transformed using a system or a vector according to the invention, the cells expressing the said gene(s) are selected and a plant is regenerated from these cells.

The most frequently used transformation methods which may be mentioned are, in particular, the methods which employ Agrobacterium, whether this be *Agrobacterium tumefaciens* or *Agrobacterium rhizogenes*, biolistic or any other techniques (electroporation, etc.).

These methods are known (REAM, W., 1989; NEGRETIU, I. and GHARTI-CHHETRI, G. B., 1991; CASSE-DELBART, F., 1996; STANFORD, J. C., 1990) and will not be described again in detail.

The technology, which in particular makes use of plasmid systems, enables a first transformation of a competent bacterial strain, in general *E. coli*, to be effected, which transformation enables the structure of the plasmids to be cloned and monitored. The strain is then used to transfer the recombinant plasmids into agrobacterial strains, which will then be used to transform the plant cells.

The plants comprising an expression system or cells according to the invention are part of the invention.

The plants which are obtained by implementing the processes according to the invention are also part of the invention.

Finally, the invention relates to plants according to the invention, characterized in that the plants are plants of agricultural interest, in particular grapevine plants.

Other characteristics and advantages of the constructs and the processes according to the present invention will be evident from the examples which follow.

BRIEF DESCRIPTION OF THE DRAWINGS

Figure Legends

FIGS. 1 and 1a: General scheme depicting the different steps in the method for isolating the inducible promoter PMs PR10-1, corresponding to the IND S1 sequence.

FIG. 2: Representation of the various clones which were isolated and which correspond to the Southern blot, which blot was hybridized with the 5' and 3' parts of cDNA-PR7, which parts were delimited by an internal BamHI (B) site which was detected in this CDNA.

Restriction sites: E=EcoRI, B=BamHI.

The values indicated in the figure are expressed in kb (kilo bases).

FIG. 3: DNA sequence corresponding to the IND S1 sequence, which is the isolated genomic sequence of the inducible lucerne promoter PMs PR10-1.

FIG. 4: DNA sequence corresponding to the sequence of a gene for grapevine stilbene synthetase which is modified by adding an adaptor (modified vst1).

The modified part is depicted in italics.

The coding and noncoding (intron) parts are depicted in upper case and lower case letters, respectively.

FIG. 5: DNA sequence comprising the sequence of the inducible promoter PMs PR10-1 (corresponding to the IND S1 sequence in lower case) linked to the sequence of a gene for grapevine stilbene synthetase which is modified by adding an adaptor (modified vst1, corresponding to FIG. 4). Between the two (framed in the sequence) are (end of the promoter in lower case and start of the gene containing the translation start codon in upper case) the 13 nucleotides which come from an internal sequence of the coding frame of the Ms PR10-1 gene; since the ATG has been positioned in reading frame with the modified vst1 gene, these nucleotides are thus integrated into the coding frame of vst1.

The sequence of the inducible promoter PMS PR10-1 includes the 7 of the 13 nucleotides of the sequence of the gene Ms PR10-1 (in lower case in the frame).

The coding and noncoding (intron) parts of the part corresponding to the sequence of the gene for grapevine stilbene synthetase are depicted in upper case and lower case letters, respectively.

Figure 6:
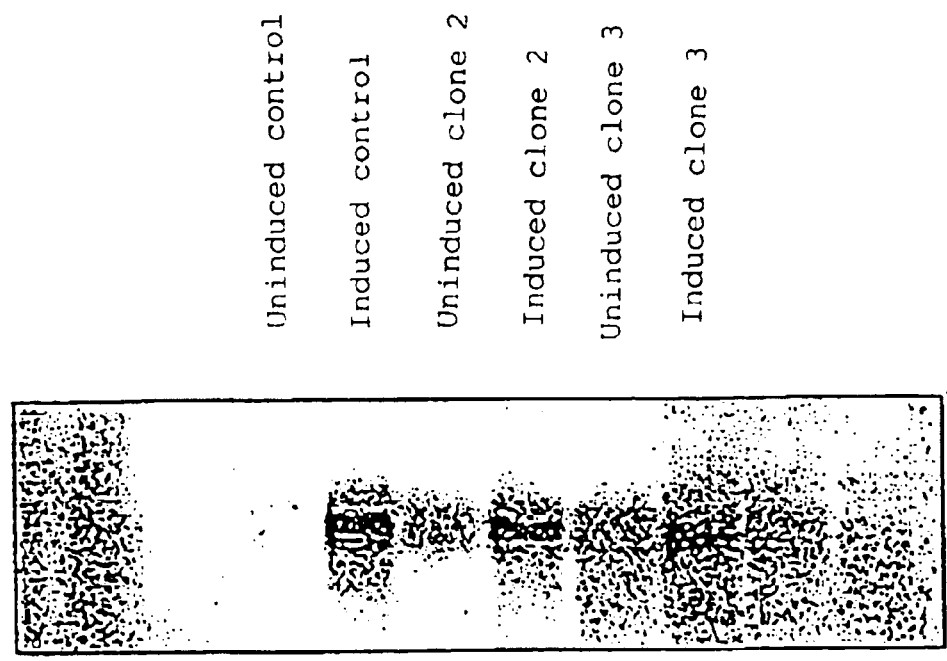

FIG. 6: Demonstration of the induction of the gene encoding a stilbene synthetase with UV light.

The RNAs are extracted from approximately 1 g of leaves 17 hours after inducing with UV light. From 10 to 20 µg are loaded onto a formaldehyde/formanude denaturing gel. After migration (3 V.cm$^{-1}$), the RNAs are transferred to a nylon membrane and fixed by exposure to UV light (254 nm, 33 mJ.cm$^{-2}$). The Northern blot is obtained by hybridizing, at 65° C. and overnight, with the biotinylated probe vst1.

The explant which is used as the starting material consists of leaves which have been isolated from 41B (control) vitroplants or 41B vitroplants which have been genetically transformed with a construct (13 kb insert comprising two complete stilbene synthetase Its genes, vst1 and vst2, a fragment of grapevine genomic DNA and another truncated grapevine stilbene synthetase gene (vst3)) which integrates supernumary copies of genes encoding grapevine stilbene synthetase under the control of their own promoters (clones 2 and 3 corresponding to clones 55-2 and 55-3, respectively). 41B: stock-vine hybrid *V. vinifera*, Chasselas H *V. berlandierii*.

Figure 7:
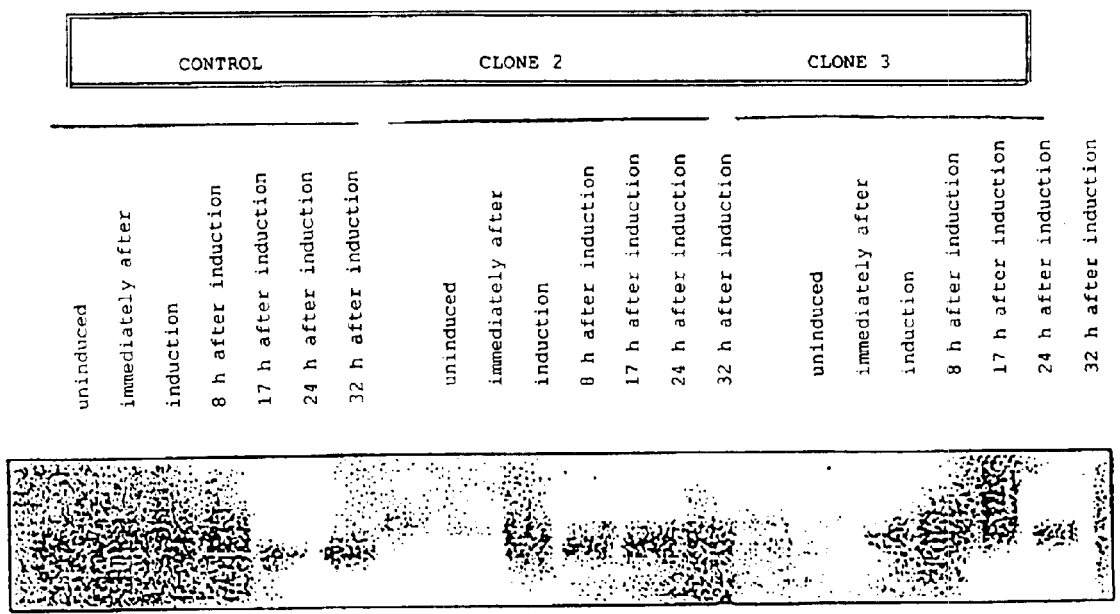

FIG. 7: Kinetics of stilbene synthetase mRNA accumulation following induction with UV light.

The RNAs are extracted from approximately 1 g of leaves. From 10 to 20 µg are loaded onto a formaldehyde/formamide denaturing gel. After migration (3 V.cm$^{-1}$), the RNAs are transferred to a nylon membrane and fixed by exposure to UV light (254 nm, 33 mJ.cm$^{-2}$). The Northern blot is obtained by hybridizing, at 65° C. and overnight, with the biotinylated probe vst1.

The explants are leaves which have been isolated from 41B vitroplants. The control is a clone which has not been transformed genetically, contrary to clones 2 and 3 (corresponding to clones 55-2 and 55-3, respectively), which have integrated, into their genome, the 13 kb insert (see above) containing genes encoding grapevine stilbene synthases (vst1+vst2). 41B: stockvine hybrid *V. vinifera*, Chasselas H *V. berlandierii*.

Figure 8:
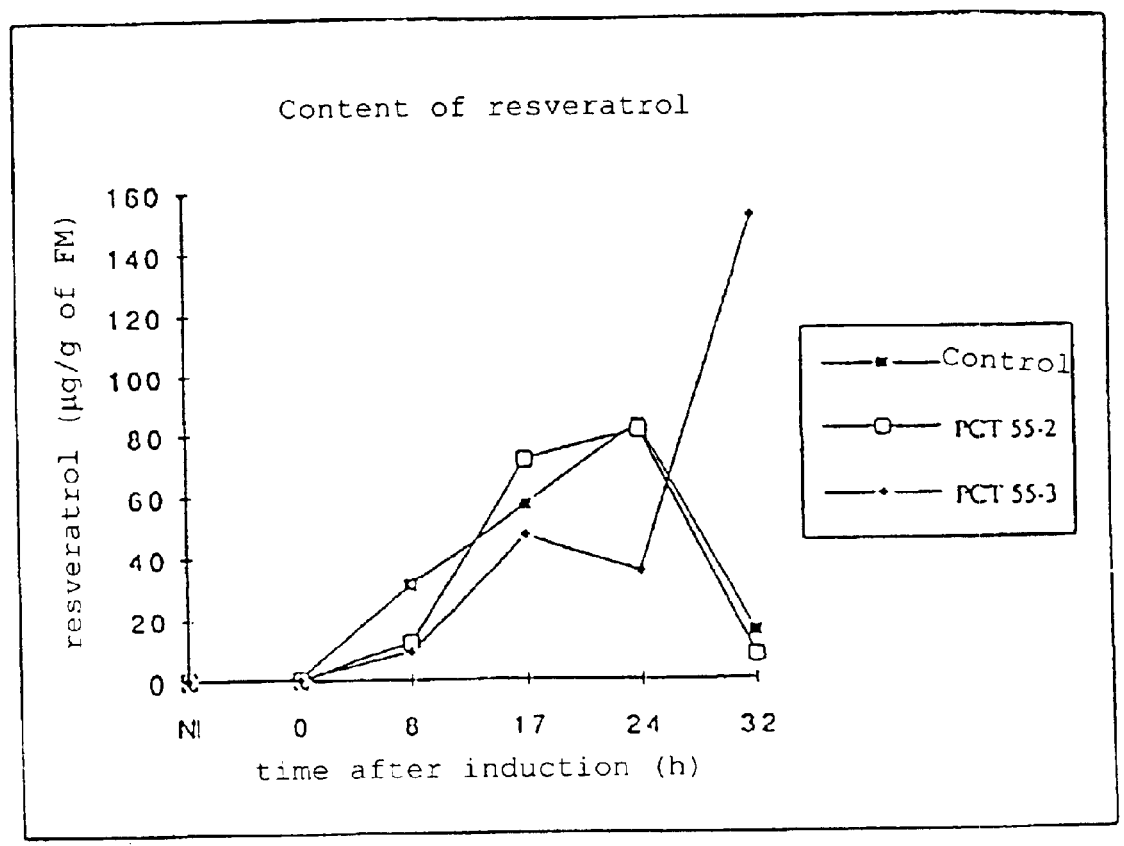

FIG. 8: Quantity of resveratrol present in vitroplant leaves which have been treated with UV light for 8 min and analysed at different periods after induction.

The quantities are expressed in μg per g of fresh material.

NI: not induced

The control consists of leaves taken from untransformed 41B. PCT 55-2 and 55-3 are two transformants which have integrated the 13 kb insert comprising two complete stilbene synthetase genes (vst1+vst2).

Figure 9:
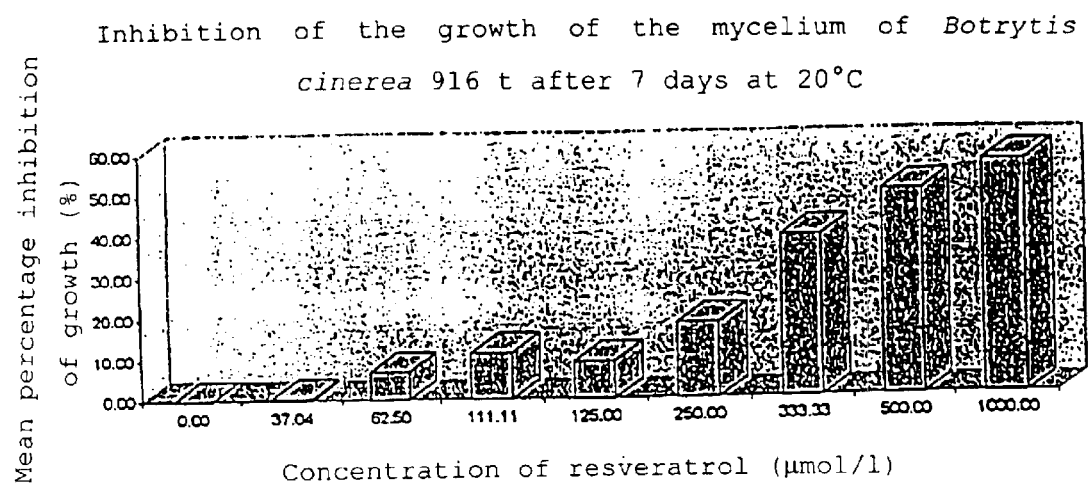

FIG. 9: Inhibition of the growth of Botrytis cinerea mycelium, strain 916T, after 7 days at 20° C.

The mycelium is cultured on a malt/glucose medium containing different concentrations of resveratrol.

FIG. 10: Photographic plate 1 Macroscopic observations which are characteristic of different varieties of grapevine in interaction with Botrytis cinerea 5 days after inoculating vitroplant leaves with a conidial suspension—untransformed plants.

Upper Row:
  Left: Folle blanche variety, clone 280, susceptible.
  Right: Pinot noir variety, clone 386, moderately tolerant.
Lower Row:
  Left: Ugni-blanc variety, clone 479, tolerant.
  Right: 41B stock-vine, tolerant.

FIG. 11: Photographic plate 2

Macroscopic observations which are characteristic of 41B stock-vine clones which have been transformed with different constructs (145: Ms PR10-1 promoter—vst1 gene; 55: 13 kb insert comprising two genes, vst1 and vst2, under the control of their own promoters), in interaction with Botrytis cinerea 5 days after inoculating vitroplant leaves with a conidial suspension.

Upper Row:
  Left: Clone 145-2.
  Right: Clone 145-5.
Lower row:
  Left: Clone 145-6.
  Right: Clone 55-3.

FIG. 12: Photographic plate 3

Fluorescence microscopy observations which are characteristic of different grapevine varieties in interaction with Botrytis cinerea 5 days after inoculating vitroplant leaves with a conidial suspension.

Fluorescence: filter unit A (excitation of from 340 to 380 nm; stop filter at 425 nm). Resveratrol gives out a bluish white and blue (depending on its concentration) fluorescence light while chlorophyll fluoresces red. The black region corresponds to the region of fungal infection or to necrotic regions when they are small.

Upper Row:
  Left: Folle blanche variety: clone 280, susceptible, little or no synthesis of resveratrol.
  Right: Pinot noir variety, clone 386, moderately tolerant. Synthesis of resveratrol in the veins and in the region of fungal maceration.
Lower Row:
  Left: Untransformed stock-vine 41B (tolerant). Synthesis of resveratrol intense in the veins and in the lamina around the small and very localized regions of infection (necrotic regions).
  Right: Stock-vine 41B transformed with construct 145, i.e. the vst1 gene promoter PMs PR10-1, clone 145-5, very tolerant. Strong synthesis of resveratrol around and in the region of infection, in veins and over almost the whole of the lamina of the leaf.

DETAILED DESCRIPTION OF THE INVENTION

EXAMPLE 1

Obtaining Genomic Clones Which Comprise Regulatory Sequences of Lucerne PR Protein Genes A) Obtaining a Probe for the Purpose of Finding the Promoters (cf. FIGS. 1 and 1a)

The incompatibility response (hypersensitivity reaction, HR) which is obtained in the lucerne (Medicago sativa) and Pseudomonas syringae pv pisi host/parasite relationship made it possible to construct a cDNA library. It was prepared from messenger RNAs which were extracted and purified from the zone adjacent to the necrosis caused by the bacterial infection. Plant material was taken 6 hours after infiltrating with the bacterial suspension.

The PR proteins in leguminous plants are known to have motifs which are conserved; it was therefore possible to synthesize oligonucleotides corresponding to these motifs defined on the basis of sequencing which had already been carried out on pea and soya bean PR proteins. PCR amplification enabled a radioactive probe to be obtained which was then used to select transcripts in the CDNA library. One of these clones, cDNA-PR7, was adopted since after sequencing it exhibited 87% homology with the genes encoding the pea and soya bean PR proteins. Analysis showed that it in fact corresponded to a gene encoding a class 10 PR protein according to the VAN LOON et al. (1994) classification. It was designated Ms PR10-1 (Medicago sativa PR class 10 protein, clone 1).

A control which was carried out on lucerne by means of Northern blotting showed that, in the incompatibility reaction, the corresponding transcript began to accumulate 3 hours after infection, passed through a maximum between 24 and 48 hours and decreased slowly from 72 hours onwards.

This fragment is characterized by the existence of an internal BamHI site (marked with a B in FIG. 2) which delimits two moieties:
  the one, termed 5' and of approximately 340 bases, includes the region upstream of the ATG (which is transcribed but not translated) and a downstream sequence corresponding to 306 bases,
  the other, termed 3', corresponds to the end of the coding moiety, i.e. 165 bases, and to the untranslated 3' region, that is 186 nucleotides from the stop codon to the beginning of the poly A.

B) Isolation of Genomic Clones Comprising Promoters of PR Proteins

1) Isolation of Genomic Clones

A lucerne genomic library, prepared in EMBL4 (titre: $7.10^8$ p.f.u. (plate-forming units)$\times ml^{-1}$), was used on this occasion and $6.10^5$ p.f.u. were plated out. Pit The 5' fragment of Ms PR10-1 (cDNA PR7) was used as a probe to screen this library and 45 clones gave a signal, which was strong for 13 of the clones. Restriction mapping and hybridization which were carried out using the 5' and 3' fragments of Ms PR10-1 led to the conclusion that there were 7 distinct clones (cf. FIG. 2). Comparison of the sizes of the 7 clones (9.3; 6.5; 6.1; 5.8; 4.8; 4.2; 2.2 kbp) which were obtained by screening the library with those of bands detected on a blot of lucerne genomic DNA showed good agreement between these two types of experimental data (cf. FIG. 2). It was therefore possible to deduce from this that the genes encoding the PR7 protein corresponded to a small multigenic family.

The fragments (EcoRI/EcoRI sites) of these clones (apart from clone C12) were then subcloned in whole or in part and sequencing was undertaken.

2) Sequencing Carried Out

One clone was chosen for sequencing first, i.e. clone C15 (cf. FIGS. 1 and 1a).

The initial sequencing work demonstrated the presence of an intron of approximately 315 nucleotides in the open reading frame of the gene encoding the PR protein. The clone under study was then analysed after having been digested with BamHI (cf. FIG. 1a).

Clone C1S: 6.1 kb

Analysis of the clone with EcoRI and BamHI enabled two fragments to be obtained, i.e. E-B (approximately 2.4 kbp) and B-E (approximately 3.7 kbp). After sequencing and comparing the coding sequence (interrupted by an intron of 600 nucleotides) with that of Ms PR10-1 (cDNA-PR7), it appeared that this genomic clone was absolutely identical to this reference CDNA.

3) Analysis of the Expression of the Isolated Clones in the Lucerne/Pseudomonas System The experiments focused on clone C15, using the 5' extension technique in order to determine the messenger molecules which were in fact transcribed during induction of the defence reactions. This technique has the additional advantage of making it possible to locate the transcription initiation site. The results demonstrated that clone C15 was in fact expressed during induction of the defence reactions in the leaves as part of the lucerne/Pseudomonas interaction.

EXAMPLE 2

Genetic Transformations which were Carried Out in Order to Verify the Promoter Activity of the Isolated Clones A) Promoter Regions Used Two promoters were used for these verificatory transformations: a control promoter and the PR promoter which was isolated from the lucerne genome and which was derived from C15 (corresponding to the PMs PR10-1 promoter).

1) CaMV-35S Promoter

This promoter, which is constitutive, is used as a standard promoter. It corresponds to the sequence for regulating the transcription of the gene for the 35S RNA subunit of the cauliflower mosaic virus (CaMV). The promoter region which was used to effect the construct with the gus reporter gene in fact corresponds to a fraction of this promoter, which fraction was reisolated in the form of an EcoRI/BamHI fragment from the plasmid pDH51 (PETRZAK et al., 1986).

2) PR Promoter

A study was carried out of the promoter regions of the C15 genomic clone. This promoter was subsequently termed PMs PR10-1.

PMs PR10-1:

It is derived from the EcoRI/BamHI (E/B) fragment of 2.4 kb of the C15 clone (FIG. 1a). The integration of this fragment into the binary plasmid upstream of the reporter gene (see below) was made difficult by the fact that there was no restriction site in clone C15 between the TATA box (initiation of transcription) and the ATG (initiation of translation). F9 Deletion experiments were therefore carried out until a fragment of approximately 1.5 kb was obtained (sequence IND S1). A BamHI site was then added, by blunt-end ligation, to the resulting fragment in order to enable it to be inserted upstream of the different coding sequences which were subsequently used. This fragment therefore comprises, expressed by reference to the cDNA which was used to clone it and also the upstream promoter region: 39 terminal nucleotides of the 5,UTR (UnTranslated Region) of the Ms PR 10-1 gene, located bp from the initiating ATG codon, the ATG of the Ms PR10-1 gene and a short fragment of its coding region (10 bp) immediately upstream of the integrated BamHI site. Taking into account the cloning sites, the promoter which is constructed in this way has a potential ATG, which could lead to the presence of two ATG codons at a short distance from each other when constructing chimeric genes. There could then be a risk of altering the coding frame of the gene which is used (reporter gene or stilbene synthetase gene).

For the transformation experiments with the reporter gene, PMs-PR10-1 (FRI) was used as such after having been cloned into the STRATAGENE Bluescript pSK+/−plasmid. It was possible to reisolate it in the form of an approximately 1.5 kb EcoRI/BamHI fragment.

3) Plasmids Used a) p35S—Gus Intron (VANCANNEYT et al. 1990)

This plasmid is a derivative of pBinl9 (BEVAN, 1984) and as such possesses the right and left borders of the binary plasmids, enabling the segment contained between these borders to be inserted into plants using agrobacteria.

The development of the gus intron (intron derived from the potato LSI gene) reporter gene made it possible to eliminate the false positives (in particular during transient expression) which were due to contaminating agrobacteria. These bacteria are not able to splice the introns.

In the standard system, this gene, which encodes a β-glucuronidase, enables a blue coloration to be obtained when a specific substrate (5-bromo-4-chloro-3-indolyl-β-glucuronide) is used. This blue colour then indicates that the analysed plant has been transformed and, as a consequence, that the coding sequence of the gene corresponding to the enzyme has been transcribed and, therefore, that the promoter which controls it has been induced.

b) pER97

This plasmid was constructed by one of the laboratories participating in the project for testing promoter efficiency (P. RATET, ISV, cited in SZABADOS et al., 1995). It has, in particular, the advantage of possessing a multiple cloning site, making it possible to effect transcriptional fusion with the coding frame of the gus gene (E. coli uid A) containing the LSI intron. It also possesses some of the characteristics of the preceding plasmid p 35S gus intron (borders for integration into the plant genome, selection gene affording resistance to antibiotics of the neomycin type: nptII gene).

The activity of the promoter can be visualized and measured by histochemical and enzymic tests of the GUS type.

4) Derivatives of pPR97

Two main constructs were made and subsequently used for transforming model plants.

a) pR97-35S

The 35S promoter, cloned into plasmid pDH51 (cf. paragraph 5 below), was excised and inserted into the multiple cloning site of pPR97, upstream of the reporter gene, in the form of an EcoRI/BamHI fragment. This plasmid is both a positive control, to demonstrate that the construct functions, and a reference since the 35S promoter was placed in the same environment as the promoter isolated from the PR protein clones.

b) pPR97-PMs PR10-1

The 1.5 kb fragment was inserted into the same cloning site as that defined above, in this case too in the form of an EcoRI/BamHI fragment.

c) pG3-3

This enabled a strong positive control for the histochemical and enzymic tests to be obtained by cloning two 35S promoters as an inverted tandem. The activator sequences of the promoters then act synergistically. The coding frame of the gus intron gene was then placed under the control of one of the two 35S promoters.

5) Preparation of Agrobacterium Strains

The different plasmids were used to transform competent E. coli strain DH5α bacteria by thermal shock in a calcium chloride medium. After selecting transformed bacteria on a medium containing antibiotic (kanamycin) and using a mini-prep to check that they were recombinant, these bacteria were then used to transfer the recombinant plasmids into Agrobacterium strains by means of triparental conjugation using the E. coli strain HB101 harbouring the autotransferable plasmid pRK2013 (DITTA et al., 1985).

Two agrobacterium strains were used: EHA 105, a disarmed Agrobacterium tumefaciens, used for regenerating transformed plants (stable transformations) and A4TC24 Agrobacterium rhizogenes, which was used to obtain the hairy root reaction and composite plants whose roots are transformed but which otherwise have a phenotype which is identical to the original phenotype.

6) Genetic Transformations on Model Plants

Two types of transformation (transient and stable) were carried out using three model plants, i.e. Nicotiana benthamiana, Medicago truncatula and Lotus corniculatus.

The results presented will in the main be those obtained with N. benthamiana.

7) Transient Transformations

This first series of experiments was carried out for the purpose of rapidly verifying that the constructs which were produced using the gus gene functioned in the eukaryotic cells.

N. benthamiana leaves were therefore excised and cocultured on an agar medium together with the different derivatives of the EHA 105 strain. Histochemical tests were then performed 48 h after the transformation and subsequently examined after incubating overnight (12 h).

The control plasmids, p35S gus intron and pPR97-35S, gave a positive GUS coloration even if this was weak in the case of the second plasmid.

This weak reactivity is without doubt due to a construction problem since a part of the polylinker had to be retained in the vicinity of the transcription initiation site and the ATG of the gus gene. Since this polylinker part encompasses a repeat sequence it can interfere with transcription of the gene.

The pPR97-PMs PR10-1 construct gave a gus gene activity which was similar to that of the 35S gus intron positive control. This promoter, which was expected to be inducible, therefore exhibited an effect which was comparable to that of a constitutive promoter.

This result can be explained as being the consequence either of the bacterial infection or the injuries inflicted on the leaves during sampling or during culturing. Since the first hypothesis cannot be verified, the experimental protocol was modified in order to decrease the stress caused to the explants (increase in the osmolarity of the coculture medium using sucrose concentrations of from 10 to 30 g.1$^{-1}$, applying a relatively high vacuum range: a relative vacuum of from 10 to 80 mm of mercury and the production of relatively severe lesions on the leaves accompanied by significant or moderate crushing of the epidermis).

The results demonstrated that the number of transformed cells increased as the pressure increased. However, a compromise should be found in order to achieve stable transformations since the large number of transient transformations which are obtained in this case frequently turn out subsequently to be lethal for the cells. The latter are then unable to give rise to cali and thus regenerate shoots and then plants. In any case, the inducible nature of the promoter is confirmed in part since, while the coloration due to the 35S-gus intron construct can be detected up to 5 days after coculturing, that obtained using pPR97—PMs PR10-1-gus intron appears more rapidly at 48 hours but then subsides very rapidly.

8) Stable Transformations a) Tobacco: N. benthamiana

A transformation series was carried out using pPR97-35S, pPR97-PMs PR10-1 and pG3-3. A substantial number of plantlets was obtained for this transformation series. An attempt was made to obtain at least 7 acclimatized plants for each of the plasmids used. However, this was not possible for p35S-gus intron, where only 5 plants were regenerated and acclimatized. The results which were obtained are compiled in Table 1.

TABLE 1

Stable transformations obtained in N. benthamiana by transforming with the Agrobacterium tumefaciens strain EH 105 and its derivatives.

| Constructs | Cali/explants cultured | Shoots obtained | Plantlets in vivo Accl. | |
|---|---|---|---|---|
| p35S-gus intron | 10 (45) | 6 (1) | 5 | 5 |
| pPR97-35S gus intron | 115/122 | 23 | 13 | 12 |
| pPR97-PMs PR10-1 gus intron | 135/139 | 27 | 20 | 7 |
| pG3-3-35S as an inverted tandem (strong promot.) | not assessed | 37 | 28 | 20 |

Legend to Table 1:

The results are expressed as the quantity obtained. Accl.: Acclimatized plantlets Number of shoots per explant: The figure in brackets corresponds to the number of shoots which were obtained at one month in the case of the first series. In this series (comprising the 35S gus intron construct), the cali were left longer on the culture medium in order to obtain a maximum number of shoots and therefore of plants to acclimatize. In the case of the second series, a sufficient number of shoots had been obtained after one month and the experiment was then stopped.

Genetic transformations: These were done in a standard manner on 1 cm$^2$ pieces of leaf lamina, which pieces were immersed in the Agrobacterium suspension for 30 seconds and then cocultured for 48 hours before being subcultured onto agar medium for cell division and caulogenesis (MURASHIGE et al., 1962), 0.1 mg.1$^{-1}$ NAA (naphthaleneacetic acid), 1 mg.1$^1$ BAP (benzylaminopurine), 400 mg.1–cefotaxime (elimination of the agrobacteria) and 70 mg.1$^{-1}$ kanamycin (agent for selecting transformed cells). Once the first shoots have ppeared (approximately one month after coculturing), hey are placed on a rooting medium which is identical the former medium except that it does not contain lant hormones.

Rapid analysis of the results in terms of the expression of the gus intron gene depending on the ature of the promoter which is situated upstream of the coding frame of the gene shows that the PMs PR10-1 promoter gives the best results of all the promoters tested. A more detailed analysis is presented below.

9) Characteristics of the PMs PR10-1 Promoter

Plasmid pPR97-PMs PR10-1-qus Intron

This promoter gave the best results with differences in the constitutive expression of the gus gene depending on the organs tested.

a) Activity in Cali

Strong constitutive expression was found. A few minutes of incubation were sufficient to obtain a positive histochemical test. The promoter is therefore strongly induced in this type of material, something which is in agreement with the results obtained by VAN LOON (1985). Cali which are cultured in vitro are in a state of stress and the PR proteins are expressed under these conditions.

b) Activity in Acclimatized Whole Plants Roots

The promoter is induced and the histochemical test is positive after 2 hours of incubation (as against hours when the 35S promoter is used). The activity of the gus gene is not uniform in tobacco roots; only the epidermis of the old parts and the apical meristem gave the blue coloration which is characteristic for the test. According to the literature, defence gene activity in the roots is also observed under conventional conditions.

Flowers

A strong constitutive activity was found in the flowers and, more particularly, in the anthers and the pollen, of all the tobacco plants which were transformed with this construct. Gus gene activity was also detected in the trichomes of the sepals and, more weakly, in the petals. These results are also in agreement with those of VAN LOON (1985), which indicate that defence genes are induced in the floral parts.

Leaves

Weak constitutive gus activity was observed in the trichomes of young leaves of adult plants. In the case of tobacco, the rosette stage with large leaves corresponds to the juvenile stage and the ageing stage to that of the formation of seeds. This weak activity was predominantly observed in the multicellular trichomes. To our knowledge, the expression of a PR protein in such structures has never been described.

While it is possible, therefore, that the isolated PMs PR10-1 promoter has a constitutive inducing activity in the trichomes of tobacco leaves (3 plants out of 7), this activity appears to be under the influence of the development stages.

In the absence of induction by a pathogen, the activity of the promoter in tobacco is therefore limited to the root, to floral parts (anthers and pollen) and to a few cells of the aerial part (basically trichomes).

EXAMPLE 3

Other Plant Species which were Transformed

1) *Medicago trunculata*

In the case of this species, an attempt was made to create composite plants, that is plants which possess, at one and the same time, a wild-type aerial part (not genetically transformed) and transformed roots.

Young germinations were used. After development of the main root, the excised hypocotyles were soaked in a suspension of *Agrobacterium tumefaciens* EHA 105 harbouring either plasmid p35S-gus intron or plasmid pPR97-PMs PR10-1-gus intron so as subsequently to obtain newly formed roots which were transformed. After one week, roots were obtained and a histochemical GUS test was carried out. For this experiment, the control consisted of young germinations which were treated in an identical manner to the previous batches (hypocotyles were excised, but were not soaked in the agrobacterial suspension).

While all the explants of the control batch formed new roots within one week, only 50% of the explants reacted, by contrast, in the case of the batches which were treated with the agrobacteria. Whatever the treatment, no root gave a positive response to the GUS test. On the other hand, even though necrosed, the base of the hypocotyles in the treated batches often reacted by giving a blue coloration (presence of tranformed cells). The necrosed part of the explants was then excised and they were set to rooting again. 50% then developed newly formed roots, some of which were to be positive to the test in a few regions.

Chimeric roots (roots containing both transformed cells and untransformed cells) were therefore obtained, with the transformed parts corresponding to cell lines which had integrated the construct into a basal stem cell.

The two constructs which were tested, i.e. p35S-gus intron and pPR97-PMs PR10-1 gus intron, gave these transformed root cell lines in 3 and 2 explants, respectively, out of the 6 which were subjected to experiment in the case of each batch.

Although the experimental model was not adapted to the topic under investigation (study of the expression of PR proteins in association with the phenomenon of nodulation by Rhizobium), it nevertheless demonstrated that the PMs PR10-1 promoter is just as functional in this plant as in the original plant (*Medicago sativa*).

2) *Lotus corniculatus*

In this case too, the experiment had the aim of studying the induction of the promoter in association with nodulation by the symbiotic bacterium *Rhizobium meliloti* NZP 2037 (PETIT et al., 1987). Composite plants were therefore produced by transforming cells of the hypocotyl of young Lotier germinations with *Agrobacterium rhizogenes* strain A4TC24 in order to obtain the hairy root phenomenon (hairy root phenotype). Once this had developed, the main roots were excised and the plantlets were placed in a liquid medium in order to amplify the development of the phenomenon. Once the plants were acclimatized, induction of the promoters in association with nitrogen fixation symbiosis was studied by putting the plantlets under nodulation conditions (BLONDON, 1964). The two promoters which were used for the study were the same as those which were used in the experiment carried out with *M. trunculata*: 35S and PMs PR10-1. Using these two constructs; less than 10% of the roots having a hairy root phenotype exhibited roots which were positive to the GUS test. Generally speaking, the roots having this phenotype gave fewer nodules than did the control roots.

In the case of those which were obtained with the construct comprising the 35S promoter, it was only the nodules which gave a positive response to the GUS test, while, in the case of the other construct (PMs PR10-1 promoter), the coloration developed over the whole of the root apart from the secondary root initiation point. Apart from that, this latter construct did not enable nodules to be obtained on the roots derived from hairy root in interaction with *Rhizobium meliloti*.

EXAMPLE 4

Study of the Hypersensitivity Reaction of Tobacco which is Transformed with the Constructs Using Promoters of the Lucerne PR Gene and the Gus Intron Gene A) Hypersensitivity Reaction in *N. benthamiana* which is Transformed with the Constructs Linking the Lucerne PR Gene Promoter and the Gus Intron Gene 1) Hypersensitivity Reaction (HR) Test The hypersensitivity reaction (HR), developed in the *N. benthamiana/Pseudomonas syringae* pv. pisi interaction, was used in this study. Transformed tobacco plants, which had incorporated the different inserts of plasmids p35S gus intron and pPR97- PMs PR10-1-gus intron into their genome, were acclimatized and then infiltrated with a suspension of *P. syringae* (ESNAULT et al., 1993) at a concentration of $10^9$ bacteria per ml. The solution was injected into the lamina using a hypodermic syringe. Using a model of this nature, the HR reaction is regarded as being well developed after 48 hours. Leaves which had been infiltrated with the bacterial suspensions were removed at 24, 48 and 96 hours after inoculation in order to assess induction of the different promoters under study using the GUS histochemical test. The same histochemical test was also used on the leaves situated below the infiltrated leaf in order to assess any possible systemic response.

2) Study of the Induction of the Promoters Under the HR Reaction Conditions a) 35S Constitutive Promoter In the case of the 35S constitutive promoter (plasmid pG3-3, for example), the inoculation with *P. syringae* did not modify the response to the test, with this response being evident after a few minutes of incubation. Therefore, infiltration with the bacteria does not alter the constitutive glucuronidase activity which is obtained with the 35S promoter.

b) Promoters of PR Protein Genes: Ms PR10-1 Promoter

As shown in Table 2, this promoter is readily inducible by pathogen attack. While the HR reaction is still not completely developed at 24 hours (48 hours for the effect to be fully displayed), the GUS test is already positive. In the case of the young transformed tobacco plants which were obtained, the coloration is weak and predominantly produced in the lamina of the infiltrated leaf.

With regard to the systemic response, i.e. the response in the leaf below the infected leaf, the coloration is only present in the lamina. The adult (having developed stems but still not having flowered) and juvenile (rosetted) tobacco plants have the same type of response, with a weak gus gene activity as determined by the histochemical test.

In the case of the older tobacco plants, either in flower or carrying seeds, the coloration which is obtained in the test is more intense, especially in the veins and the trichomes of the infected leaf, with coloration only being present in these tissues in the case of the systemic response.

These observations therefore demonstrate differences in the expression of the reporter gene depending on the age of the plant. This response, which is dependent on the developmental stage of the plant, was found in most of the studies carried out on plant PR proteins. Induction of the PMs PR10-1 promoter is a transient phenomenon since expression of the reporter gene is no longer evident at 96 hours after inoculating the bacteria.

The induction is not limited, either, to the HR reaction which is obtained in the plant/bacterium interaction. The same type of response was obtained with the PMs PR10-1-gus intron construct when one of the explants was infected with a fungus. Homogeneous expression of the gus gene was then evident over the entire infected leaf apart from the contaminated region, which was necrosed.

TABLE 2

Induction of the different promoters under study in association with the HR reaction between *N. benthamiana* and *P. syringae*.

| Construct | 24 h after inoculation | | 96 h after inoculation |
|---|---|---|---|
| | Infiltrated leaf | Leaf below | Infiltrated leaf HR reaction |
| PMs PR10-1 | 6/7 | 6/7 | 0/3 |
| pG3-3 (35S) | 3/3 | 3/3 | 2/2 |

Legend to Table 2:

The results are shown as the number of plants responding positively to the GUS histochemical test as compared with the number of plants which were analysed.

B) Quantitative Expression of the Gus Intron Gene Under the Control of the Different Promoters The method is based on an enzyme test.

The method employs:

a) a crude extract of the enzyme encoded by the gus gene, with the enzyme being obtained from transformed tobacco plants, and b) a substrate, i.e. p-nitrophenyl-glucuronide. The rate at which the substrate is hydrolysed is monitored in a spectrophotometer and is related to the total quantity of protein in the extract. On the other hand, since it is not very sensitive, the method requires the presence of a strong promoter upstream of the gus gene.

As a consequence, it was not used for assays which required 12 hours or more of incubation with the substrate which was used for the histochemical test (X gluc: 5-bromo-4-chloro-3-indolyl-β-glucuronide).

Under these experimental conditions, the 35S promoter, located in plasmid pG3-3, gave a rate of substrate hydrolysis (expressed in arbitrary units) which was 5 times greater than that achieved using the PMs PR10-1 promoter, which was located in plasmid pPR97. On the other hand, the PMs PR10-1 promoter gave a stronger expression of the gus gene than did the 35S promoter when the latter was located in plasmid p35S-gus intron. In fact, no substrate hydrolysis was detected in this latter case.

Similarly, it was not possible to obtain spectrophotometrically detectable values when the other constructs were used.

EXAMPLE 5

Isolation of the DNA Corresponding to a Stilbene Synthetase Gene and Expression of Stilbene Synthetase Two methods were used for obtaining a gene encoding grapevine stilbene synthetase. On the one hand, data in the literature (WIESE et al., 1994) allowed the sequence of a gene to be obtained. On the other hand, a genomic insert of approximately 13 kb was supplied by BAYER AG (Agrochemical Division Research/Biotechnology-Pflanzenschutzzentrum, MONHEIM, D-51368 LEVERKUSSEN). It is specified that the company BAYER has deposited with the Deutsche Samnlung von Mikroorganismen (DSM), in Germany, strains of *E. coli* containing plasmids bearing grapevine stilbene synthetase genes (cf. EP-464 461): *E. coli* strain Fier 1 pvst 1 (DSM 6000, deposited on 18 Jun. 1990), *E. coli* strain Fier 2 pvst 2 (DSM 6003), deposited on 18 Jun. 1990) and *E. coli* strain Fier pVst 1 2 to 3 (DSM 6346, deposited on 11 Feb. 1991). BAYER has also deposited the *E. coli* strain Nurdug 2010 (DSM 4243, deposited on 17 September 1997) which contains the plasmid pGS 828.1 which bears a groundnut stilbene synthetase gene (cf. EP-309 862). The insert used for carrying out the work reported below in fact corresponds to a complex genomic clone which comprises two complete functional stilbene synthetase gene sequences (vst1 and vst2 genes) and an incomplete vst3 sequence. Subsequently, the sequence of the vst1 gene was chosen for incorporation into the constructs produced. It corresponds to a 4.9 kb genomic fragment (functional sequence including the promoter) which does not possess any restriction sites which are suitable for cloning it directly into the plasmids which are usually used as transformation vectors. Additional sites were therefore added to it by carrying out an intermediate cloning in a plasmid termed pCDNA II.

A) Addition of Supplementary Sites by Intermediate Cloning in a Plasmid pCDNA II The abovementioned genomic fragment of the vst1 gene was isolated from the original plasmid in which it had been cloned in the form of an EcoRI/PstI fragment (2.1 kb) and cloned again into a plasmid pUC19. Having been cloned, the vst1 fragment was incorporated into the same sites (EcoRI/PstI) of plasmid pCDNA II in order to change the restriction sites, delete the terminator of the gene and enable a BamHI/BamHI (1.8 kb) insert to be isolated. It was this fragment, corresponding to the open reading frame of the gene, which was used for making the constructs with the different promoters including those isolated from the lucerne genomic library (cf. FIG. 4). This insert was then cloned into pBIN 19 after using Southern blotting to verify the sizes of the different fragments which were obtained after digestion with appropriate restriction enzymes.

B) Study of the Expression of the vst1 Gene In order to verify the expression of the genes encoding stilbene synthetase in the grapevine plants, a probe (1.8 kb) encompassing the vst1 gene was prepared from plasmid pCDNA II, which had been multiplied in the bacterium *E. Coli* HB 101. The probe was then biotinylated by random priming, using the Polar Plex kit (Plex chemiluminescent kits, Millipore) in order to enable genes or transcripts encoding a stilbene synthetase to be detected by chemiluminescence on Southern and Northern blots carried out using nucleic acids which were extracted from control or transformed grapevine plants.

1) Use of the vst1 Probe for Analysing Genomic DNA Extracted from Grapevine 41B (*V. vinifera* Chasselas×*V. berlandieri* Hybrid; Stock-vine)

Southern blot analyses were carried out after extracting genomic DNA and then digesting it with EcoRI. Use of the vst1 probe enabled a large number of bands (approximately 15) to be obtained. These bands in fact correspond to fragments which contain sequences encoding a stilbene synthetase and which constitute a multigenic family (from 6 to 8 genes according to WIESE et al., 1994). Of these, vst1, vst2 and vst3 exhibit strong homology with each other. Furthermore, other genes can be recognized by this probe, in particular those corresponding to the chalcone synthetase multigenic family. This is because the two enzymes have the same structure and are of the same size (dimers of subunits of from 41 to 44 kb in size). They also use the same substrate and their amino acid sequences exhibit a high degree of homology, at least with regard to the active site.

The DNA of two plasmids was extracted for the purpose of verifying whether such a cross-hybridization was possible. One of the plasmids, pCDNA II, contained the vst1 gene while the other, pPCV 002, contained a Rosier chalcone synthetase gene, available in the laboratory. A biotinylated probe corresponding to the Rosier chalcone synthetase gene was also prepared. The Southern blots obtained by carrying out cross-hybridization showed that the vst1 probe actually recognized the Rosier chalcone synthetase fragment, and vice versa. The emitted signals are then weaker in this case of cross-hybridization.

2) Assay of Resveratrol Using Grapevine Plant Leaves

The fresh plant material, leaves or stalks, is reduced to powder in a mortar containing liquid nitrogen, and the apolar compounds are extracted with methanol (1 ml per 100 mg of fresh material: f.m.).

After centrifugation to remove debris, the methanol extract is filtered through a 0.45 µm filter and then evaporated to dryness under nitrogen. The residue is taken up in pure methanol (100 µl/100 mg f.m.). In order to remove pigments (in particular chlorophylls), the sample is then passed over a C18 column (Sep-pack WATERS), which has been pre-equilibrated with methanol. The qualitative and quantitative analysis of the extracts is carried out by H.P.L.C. (High Pressure Liquid Chromatography) on a WATERS H.P.L.C. (Model 600 E) coupled to a diode-array detector (Model 990. WATERS). The chromatography support is composed of a reverse phase C18 column (C18 ultra base, 205×4.6 mm, 5 µm; Shandon). The analysis of the extract compounds is carried out under isocratic conditions, the mobile phase consisting of a 35/65, V/V, acetonitrile/water mixture with a flow rate of 1 ml×min$^{-1}$.

An absorption spectrum is performed every two seconds between 200 and 400 nm, and the resveratrol is detected at its adsorption maximum at 305 nm.

The quantification of the resveratrol is carried out by external calibration using a standard straight line obtained by chromatography of solutions at 5, 10, 20, 50 and 100 µg·ml$^{-1}$, carried out with commercial resveratrol (Sigma). The resveratrol concentration, which is measured from the area under the peak corresponding to the molecule, is related to the unit mass of f.m. or of d.m. (dry matter) or chlorophyll mass of the sample assayed.

EXAMPLE 6

Nucleic Acid Constructs Which Link the Gene Encoding a Grapevine Stilbene Synthetase to Different Promoters 1) Constructs using constitutive promoters Two related promoters were used for making the genetic constructs permitting constitutive expression.

In the first construct, the DNA of grapevine stilbene synthetase (vst1) was placed under the control of a regulatory sequence which consisted of a cassette containing two CaMV 35S promoters arranged in series (in the same orientation). A 35S polyadenylation sequence as also added to the end of the sequence encoding the vst1 gene. The chimeric construct which was made in this way can therefore be summarized as follows: (CaMV) p35S–(CaMV) p35S–vst1–(CaMV) 35S poly A In the second construct, the vst1 coding sequence was placed under the control of four enhancer sequences, which sequences were isolated from the CaMV 35S promoter and arranged in series upstream of the CaMV 35S promoter and the native enhancer sequence of the promoter of the grapevine gene (vst1). The two chimeric sequences which were produced in this way were first of all inserted into the plasmid PMP 9ORK and the plasmids were then subsequently incorporated into the Agrobacterium strain GV3101.

These two regulatory sequences are regarded as being "strong" constitutive promoters.

2) Homologous Construct Using the 13 kb insert (vst Genes Under the Control of Their Native Promoters)

The grapevine genomic DNA fragment of approximately 13 kb in size was described above. It encompasses, in particular, two functional genes (vst1 and vst2) encoding the stilbene synthetase enzymes and one incomplete (non-functional) gene (vst3). This grapevine sequence was cointegrated into a plasmid pGV3850, which was then introduced into an Agrobacterium strain. The sequence therefore corresponds to the open reading frames of vst (grapevine stilbene synthetase) genes under the control of their native promoters.

Several series of 41B plants, which were transformed with the plasmid containing the 13 kb fragment, were obtained and were studied and analysed by Southern blotting using three different probes (1.8 kb probe from the nptll gene; 2.4 kb probe from the gene for resistance to ampicillin and 1 kb probe from the lefthand border of plasmid pBIN 19, comprising the final integration sequence of the TDNA). The majority of the plants which were used reacted to one or other of these probes. These clones were numbered according to a code: 55 for the construct and 2, 3, 5, 6, 7 and 9 for the different transformants which were obtained.

3) Constructs Using the Inducible PMs PR-10-1 promoter

The construct containing the PMs PR-10-1 promoter, which was isolated from lucerne genomic PR clones, was made (cf. FIG. 5).

Construction of the Plasmid pBin 19 - PMs PR-10-1-vst1 -35S Terminator Gene

Since the PMs PR10-1 promoter which is isolated from lucerne and the vst1 gene each contain a translation-initiating ATG codon, an adaptor was made in order to clone the vst1 gene into the construct without an additional ATG. This adaptor was synthesized in the form of two oligonucleotides of 11 bp in each case, one of which was BamHI-compatible while the other was MunI-compatible. The adaptor was then incorporated into the MunI site of the vst1 gene which was cloned into the plasmid pUC19. The insert was then recovered by digesting with BamHI, after which it was cloned into pBIN 19 between the PMs PR10-1 promoter and the 35S terminator. The insert of the vst1 gene, together with its adaptor, is therefore located between the PMs PR10-1 promoter and the 35S terminator. Under these conditions, the ATG of the vs t gene was removed and 3 additional codons were included in the vst1 coding frame upstream of the gene. It was checked by sequencing that the open reading frame of the gene was still in phase with the remainder of the construct.

After having transformed 41B plants with the insert containing, inter alia, the chimeric sequence: PMs PR10-1-promoter-vst1 gene 35S terminator, the transformants were analysed by Southern blotting using the nptII probe which has already been described. Nevertheless, it is not fully possible to demonstrate complete integration using this method and, in particular, this probe, since, in the Agrobacterium system, it is accepted that insertion into the genome of the plant begins at the right-hand border and terminates at the left-hand border. Since, in the construct which is used, the nptII gene is located close to the right-hand border, it is therefore possible for the integration to be partial, with the nptII gene being inserted but with there being a subsequent block in integration before the left-hand border is reached.

The transformants were coded 145 and allocated the numbers 2, 5 and 6 for those transformants whose results are presented below.

EXAMPLE 7

Genetic Transformation of the Grapevine and Analysis of the Efficiency of the Promoters Being Studied As described above (Example 6), four main constructs were produced for transforming the 41B stock-vine (V.vinifera×V. berlandieri) laboratory model system. The reason for using the latter system is that it has the advantage of giving good results in the transformation of embryogenic cell suspensions with agrobacteria. Approximately 50 transformants are obtained on average in experiments using from 0.1 to 1 µl P.C.V. (packed cell volume) of embryogenic cells. Furthermore, selection, development of the transformed embryos and regeneration into plants are all rapid. Plantlets having from 6 to 8 well-developed leaves can be obtained in vitro in two months of culture.

A) Genetic Transformation of 41B with Vectors Containing the vst1 Gene Under the Control of Constitutive Promoters Two constructs were tested, the one containing the 35S double promoter arranged in series upstream of the vst1 gene and the second consisting of a regulatory sequence composed of 4 CaMV 35S enhancer sequences arranged in series upstream of the CaMV 35S promoter, with the whole being located upstream of the vst1 gene possessing its native enhancer sequence. Four trial series were performed (two for each of the constructs) with the aim of transforming the embryogenic grapevine cells. None enabled plants or even embryos to be regene-rated. In every case, rapid necrosis of the embryogenic cell suspensions was obtained after the 48 hours of coculture with the agrobacteria. These constructs cannot be used to obtain transformed plants which are constitutively expressing the vst1 gene under the control of these "strong" promoters. One hypothesis may be put forward; it is possible that expression of this gene blocks the regeneration into embryos due to the Irapid necrosis of the potentially embryogenic cells in response to the production of stilbenic phytoalexins.

These negative results, which were obtained with the constructs containing constitutive promoters of 35S type, demonstrate the importance of controlling overexpression of the vst1 gene by means of a homologous or heterologous promoter which can be induced, in particular, by a pathogen.

These present results are similar to those which were published by FISHER and HAIN in 1994 and which underline the fact that they did not succeed in constitutively expressing the groundnut stilbene synthetase gene at an elevated level in tobacco when using the CaMV 35S promoter. According to these authors, when such a construction is used, expression of the gene would be regulated negatively when the plant is attacked by a pathogen. This regulation, according to their hypothesis, could result from the deployment, by the plant, of defence mechanisms which are normally induced by the pathogens (synthesis of PR proteins, in particular) and which would exert an inhibition on the viral promoters. ps B) Genetic Transformations of 41B with Vectors Containing the vst1 Gene Under the Control of Promoters which can be Induced by Abiotic and/or Biotic Stresses 1) Study of the expression of the vst genes, and of their kinetics of induction with UV light, in excised leaves which are isolated in the surviving state, and in whole-plant control 41B grapevine vitroplants or 41B grapevine vitroplants or which are transformed with the 13 kb insert It has been demonstrated that the synthesis of resveratrol (main grapevine phytoalexin), which is a product of the reaction catalysed by an enzyme stilbene synthetase can be induced by ultraviolet (UV) light, that is under conditions of abiotic stress (LANGCAKE et al., 1977; SBAGHI et al., 1993). Under normal conditions, grapevine synthesizes little or no resveratrol; by icontrast, following induction with U.V. light (10-minute exposure to UV light at 254 nm, for a lamp dissipating 600 $\mu W.cm^{-2}$), followed by a period of 20 hours in the dark, the phytoalexin is synthesized in the excised leaves.

a) Method Used Irradiation of the leaves:

leaves of vitroplants: at 254 nm for a lamp dissipating 600 pW.cm$^{-2}$ vitroplants for 13 minutes, leaves isolated from vitroplants or at 254 nm for a lamp dissipating 600 gW.cm$^{-2}$ for 8 minutes, extraction and analysis of the mRNA from the plant material and estimate of the resveratrol by fluorescence after excitation at 365 nm at a given time after induction.

Each sample consists of 3 leaves which have been isolated from the same plant and which have been separately induced by UV light but then recombined for the extraction and assay. The test is performed on excised leaves, which have been isolated from vitroplants or on vitroplants which are being cultured on agar medium and which possess from 6 to 7 well-developed leaves. The three oldest leaves on each plantlet are removed and used for the test. The upper surface of the leaves is exposed to the UV light. Following analysis, the quantities of resveratrol obtained are expressed in $\mu g$ of product either per gram of fresh weight of analysed leaves or per gram of dry matter (estimated on the pellet after centrifuging and after extraction with methanol) or in mg of resveratrol per g of chlorophyll.

The tables given below show the values which were obtained for the 41B and 55-X clones, which were transformed with the 13 kb genomic clone construct in which two genes, i.e. vst1 and vst2, both of which genes are under the control of their native promoters, are present in the sequence used as insert.

b) Study of Abiotic (UV light) Stress on Excised Leaves (Experiment No. 1)

The results, corresponding to construct 55 (13 kb insert) and to clones 2 (55-2) and 3 (55-3), are presented in Tables 3 and 4 below (assay of resveratrol) and depicted in FIGS. 6 and 7 (analysis of the transcripts). The study of the kinetics of the induction by UV light of the expression of the genes encoding stilbene synthetase was performed after a period which separated the induction with UV light from the analyses and which was either fixed at 17 hours (cf. Table 3 and FIG. 6) or was a variable period of 0, 8, 17, 24 or 32 hours after induction (cf. Table 4 and FIGS. 7 and 8).

TABLE 3

Quantities of resveratrol which are detected in uninduced control and transformed leaves or in control and transformed leaves at 17 hours after induction with UV light (expressed in $\mu g \cdot g^{-1}$ of fresh material)

| Untransformed controls | | Clone 55-2 | | Clone 55-3 | |
| --- | --- | --- | --- | --- | --- |
| Uninduced | Induced | Uninduced | Induced | Uninduced | Induced |
| 0 | 12 | 0 | 11 | 0 | 13 |

Legend to Table 3:

The leaves were excised from 41B vitroplants prior to induction with UV light. Clones 55-2 and 55-3 correspond to transformed plants which have integrated an insert of 13 kb which contains genes encoding stilbene synthetase.

The fluorescence, which is observed in the blue/violet band at approximately 450 nm, is very strong in the veins of the excised leaves and is distributed uniformly over the entire surface of the leaf. The control leaves, which have not been induced with UV, do not exhibit any fluorescence. These results demonstrate specific expression of the genes encoding stilbene synthetase. Analysis of the transcripts by means of Northern blotting, which was carried out using the vst1 probe, demonstrates the presence of a fragment of approximately 1.8 kb in size whose emitted signal is very intense in the case of the leaves induced with UV light but which is absent or very weak in the case of the uninduced plants (cf. FIG. 6).

TABLE 4

Kinetics of the development of resveratrol concentrations in 41B vitroplant leaves which have been induced with UV light, removed from the plants being cultured on agar medium, and then isolated and analysed for their resveratrol content at various periods after induction.

| Time after induction | Quantity of resveratrol (in $\mu g \cdot g^{-1}$ of fresh material) | | |
| --- | --- | --- | --- |
| (h) | Control | PCT 55-2 | PCT 55-3 |
| NI | 0 | 0 | 0 |
| 0 | 0.6 | 0 | 0 |
| 8 | 30.8 | 12.1 | 9 |
| 17 | 56.8 | 71.7 | 47 |
| 24 | 83.2 | 81.4 | 35.2 |
| 32 | 15.5 | 7.7 | 151.8 |

Legend to Table 4:

The results are expressed in $\mu g.g^{-1}$ of fresh material. Two plants, transformed with PCT 55-2 and PCT 55-3 respectively, were analysed in comparison with the control.

NI: Not Induced with UV Light.

Under these conditions, after stressing with UV light, the quantity of resveratrol found in the control leaves is at a maximum at 24 hours after induction (of the order of 80 $\mu g.g^{-1}$ of f.m. for 41B). However, there are significant variations depending on the date of the analysis in the cycle of subculturing the vitroplants: micropropagation cycle.

The results obtained after Northern blot analysis using the vst1 probe are depicted in FIG. 7. At least two types of transcripts, of very similar size (approximately 1.8 kb), were detected. Although cross-hybridization with a chalcone synthetase transcript cannot be excluded, the different messenger RNAs which were recognized probably correspond to the expression of different stilbene synthetase genes. Thus, it has been shown in the grapevine (WIESE et al., 1994; KINDL, personal comnsication) that differences exist in the kinetics of induction of the different genes of the multigenic family encoding stilbene synthases.

Northern blot analysis demonstrated that, in the leaves which were excised from grapevine 41B and then subjected to the abiotic stress which exposure to UV light represents, the stilbene synthetase transcripts exhibit an expression maximum at approximately 17 hours to 32 hours after induction. These results are comparable with those obtained with grapevine cell cultures, which also demonstrated the same pattern of expression but with the presence of two maxima (WIESE et al., 1994).

c) Study of Abiotic Stress (UV light) in the Isolated Surviving Leaf (Experiment No. 2), Induction in Vitroplants Before Isolation of the Leaves Table 5 below presents the results which were obtained for a second series of transformants which had integrated the 13 kb insert. The study of the kinetics of the induction, with UV light, of the expression of the genes encoding stilbene synthetase was performed after a variable period, separating the induction with UV light from the analyses, of 20, 40 or 60 hours.

TABLE 5

Concentration of resveratrol in the isolated leaves of grapevine vitroplants after induction with ultraviolet light and extraction at different survival times.

| Clone studied | Survival time of the leaves isolated from vitroplants after induction with UV light (8 min at 254 nm) and before extraction of the resveratrol | | |
|---|---|---|---|
| | 20 hours | 40 hours | 60 hours |
| 41B - control not induced | 0 | 0 | 0 |
| 41B - control induced | 281 | 165 | 6 |
| Clone 55-2 induced | 135 | 918 | 58 |
| Clone 55-3 induced | 44 | 931 | 301 |
| Clone 55-5 induced | 392 | 83 | 657 |
| Clone 55-6 induced | 339 | 235 | 43 |
| Clone 55-7 induced | 263 | 411 | 148 |
| Clone 55-9 induced | 386 | 823 | 54 |

Legend to Table 5:

The concentrations of resveratrol are expressed in $\mu g^{-1}$ of dry matter.

41B stock-vine hybrid *V. vinifera* Chasselas×*V. Berlandierri*.

The results presented in Table 5 enable two groups of plants to be distinguished:

The first corresponds to the control and to two of the transformants, i.e. 55-6 and 55-7. In general, they exhibit a maximum resveratrol concentration of between 280 and 410 $\mu g^{-1}$ of dry material, with this maximum generally being at 20 hours after induction, except for clone 55-7, when it is at 40 hours.

The second group exhibits maxima which are higher, that is almost double those of the first group (from 820 to 930 $\mu g.g^{-1}$ of dry material). This group consists solely of transformants (55-2, 55-3 and 55-9). The maximum is expressed at 40 hours after the induction with UV light; on the other hand, at 20 hours after induction, these plants frequently have concentrations which are much lower than those of the first group. This is the case, for example, for clones 55-2 and 55-3 (135 and 44 $\mu g.g^{-1}$ of dry material, respectively). However, one of the clones, i.e. 55-9, is of interest since it exhibits resveratrol concentrations which are greater than those of the control in all cases (386, 823 and 54 $\mu g.g^{-1}$ of dry material at the times of 20, 40 and 60 hours after induction).

In this surviving leaf system, an uninduced control never exhibits resveratrol and, in almost all cases (apart from clone 55-5, which behaves in a distinctive manner), the resveratrol concentration falls drastically at 60 hours after induction.

d) Study of Abiotic Stress (UV light) which is Carried Out on Vitroplants which are Being Cultured on Agar Medium This study, which is carried out on a plant which is growing on an agar medium, makes it possible to analyse the production of resveratrol when other defence mechanisms of the plant may be being expressed, at least those mechanisms which are capable of being expressed under the in-vitro culture conditions. Furthermore, the study makes it possible to monitor the synthesis of resveratrol over a longer period (in the preceding studies, the isolated leaf necroses beyond 72 hours).

Four transformed 41B vitroplant clones in culture (55-2, 3, 5 and 6) were treated with UV light under the same conditions as before (8 min at 254 nm), with the leaves only being removed from the plant at 20 hours after induction. The results which were obtained were compared with the untransformed control as well as with a clone of *Vitis rupestris* and with 3 clones of *Vitis vinifera* variety which are known in the field for having a relatively high susceptibility to attacks by Botrytis on their berries.

The literature (SBAGHI et al., 1993) in fact demonstrates that a correlation exists between the susceptibility of the berries to Botrytis, as assessed in the vineyard, and the content of resveratrol in the leaves of vitroplants which had been induced with UV light. The results are presented in Table 6 below.

TABLE 6

Results of HPLC assays of resveratrol which were performed at 20 h after inducing several different varieties of grapevine with UV light of 254 mn for 8 min.

| Variety tested | (resveratrol) $\mu g \cdot g^{-1}$ of dry weight |
|---|---|
| Rupestris 215 | 351 |
| Stock-vine 41B | 237 |
| Ugni-blanc 479 | 209 |
| Pinot noir 386 | 86 |
| Folle blanche 280 | 37 |
| Pct 55-2 | 361 |
| Pct 55-3 | 235 |
| Pct 55-5 | 115 |
| Pct 55-6 | 539 |

Legend to Table 6:

The induction with UV light is performed on vitroplants which are being cultured on agar medium. The leaves are removed and extracted for analysis at 20 hours after the treatment. PCT 55-2, 3, 5 and 6-transformants which have integrated the 13 kb insert into their genome. The results show the average of 3 repetitions.

These results provide a good indication that a correlation exists among the varieties and grapevine plants between susceptibility to Botxytis and content of resveratrol in the leaves at 20 hours after induction. Two groups can be identified in the untransformed varieties and grapevine plants. The first, which is formed by *V. ruspestris*, *V. vinifera*×*V. berlandieri* (41B) and Ugni-blanc, corresponds to those which are relatively tolerant to the fungus. The second, consisting of the Pinot noir and the Folle blanche, represents those which are regarded as being moderately tolerant to very susceptible (Folle blanche for example).

As far as the transformants are concerned, they have, on average, resveratrol contents at 20 hours after induction which are greater than or equal to the untransformed 41B control (539, 362 and 236 $\mu g^{-1}$ of dry material for clones 55-6, 55-2 and 55-3, respectively, and 237 for the control).

By contrast, the concentration obtained in the case of the transformed clone 55-5 is half that of the control. If these values, expressed in µg-1 of dry weight, are compared with those of the isolated leaves (Table 5), it is seen that they are similar in the case of the control but that, on the other hand, variations exist in the case of the transformants which are analysed at 20 hours after induction. These variations are at times very substantial (135 for induction in isolated leaves and 362 for induction in vitroplants in the case of clone 55-2; 44 against 236 in the case of clone 55-3; 392 against 116 in the case of clone 55-5 and 339 against 540 in the case of 55-6). In addition, a great variability exists among the various repetitions.

2) Comparative study of the expression of the vst gene and of its kinetics of induction by biotic stress in 41B grapevine vitroplants which have been transformed with the 13 kb insert and with the construct comprising only the vst1 gene under the control of the PMs PR10-1.

The results above (chapter 1), which were obtained in vitroplants which had integrated, by genetic transformation, additional copies of stilbene synthetase genes (in the form of a 13 kb insert comprising two functional vst1 and vst2 sequences), show that an overproduction of resveratrol, which is produced from the reaction catalysed by the stilbene synthetase enzyme, is possible in some transformants when these genes are elk under the control of their own promoters, and in response to an abiotic stress such as U.V. irradiation.

The production of resveratrol was then verified with respect to these results, in two types of transformant, the first representing a 41B clone which had integrated the 13 kb insert (vst1 and vst2 stilbene synthetase genes under the control of their own promoters), the second representing several clones which had incorporated only the vst1 gene under the control of the lucerne defence gene regulatory sequence PMs-PR10-1. This comparison was carried out after induction by a biotic stress caused by *Botrytis cinerea*.

a) Methods Used

α) Demonstration of the fungitoxic effect of the Resveratrol Molecule on *Botrytis Cinerea*

The data in the literature with regard to the fungitoxic nature of the molecule are contradictory. According to DAÏ(1994), resveratrol does indeed exhibit an inhibitory effect on the development of the zoospores of *Plasmopora viticola* (agent of mildew); by contrast, PONT and PEZET (1990) maintain that it does not block germination of *Botrytis cinerea* conidia.

A study was carried out of the action of the molecule on the growth of mycelial hyphae of *Botrytis cinera* in culture on a malt/agar medium containing a resveratrol dilution range of from $10^{-1}$ M to $3.7.10^{-3}$ M, with the hyphae being incubated at ambient temperature for 7 days. The results demonstrated that the molecule had an inhibitory effect ($IC_{50}$=500 µmol.l$^{-1}$), with an exponential decrease in the mean growth diameter of the fungus for concentrations greater than 125µmol.l$^{-1}$. On the other hand, concentrations of 37 µmol.$^{-1}$ only have a very slight inhibitory activity on the growth of the mycelium (cf. FIG. 9). However, this inhibition increases progressively after 7 days of culture under these conditions, which are otherwise very favourable to the growth of the fungus. After 20 days, the fungus finally infects the whole of the culture surface.

β) Screening Test for the Tolerance of Grapevine Vitroplants to *Botrytis cinerea*

The implementation of the test consisted in inoculating the leaves of plantlets, which were being cultured in vitro on micropropagation medium, by depositing 20 µl of a suspension of conidia, containing $1.10^{-4}$ conidia/ml (200 conidia per deposition) in malt/glucose medium on their upper surface. The plantlets, four different leaves of which had thus been inoculated, were then cultured in a climate chamber (photoperiod: 16 h day, 8 h night; temperature: 24° C.; humidity: 70%). Two days after the inoculation, the leaves of row 4, i.e. the youngest leaves, were inspected (the necroses and macerations which were present were counted using a camera which was linked to a television monitor) and extracted with methanol in order to assay the resveratrol which had been synthesized in response to the Botrytis attack. At 5 days, the number 2 leaves were removed for observation by fluorescence microscopy. Macroscopic observation (necroses and macerations in the leaves) and counting of the leaves exhibiting fruiting bodies of the fungus (conidiophores) were also performed on the number 3 leaves. Finally, at 9 days, leaves which were interacting with the fungus, and which had been removed from three different plants, were extracted with methanol in order to assay the resveratrol. γ) Induction of Biotic Stress by Depositing a Suspension Containing *Botrytis cinerea* Spores on Vitroplant Leaves-test of tolerance to Botrytis This direct confrontation test was performed using the technique which has already been described (cf. the preceding paragraph). The same applies to the observations which were made. Four vitroplants were used for each variety or transformed clone and, in the case of each of these vitroplants, three leaves which had developed in rows 2, 3 and 4 were inoculated with the conidial suspension (200 conidia in 20 µl of malt/glucose medium). 12 inoculations were therefore performed for each variety or clone and the following analyses and observations were made:

→ Two Days After Inoculation:

inspection of the leaves in row 4 for foliar symptoms (fungal maceration zone or necrotic spots, which consist of small blackish brown regions which are located around the fungal spores, or without visible symptoms) and, assay of resveratrol in the same leaves.

→ Five Days After Inoculation:

inspection of the leaves in row 3 for foliar symptoms with counting of those leaves which carry conidiophores (fruiting bodies of the fungus) and fluorescence microscopic inspection of the leaves in row 2 in order to locate the regions of resveratrol synthesis.

Nine Days After Inoculation:

assay of resveratrol in three leaves which are derived from three different plants and which are interacting with the parasite.

For each experimental series, three *Vitis vinifera* varieties having different susceptibilities to Botrytis attack on their leaves were studied: Folle blanche (susceptible), Pinot noir (moderately tolerant) and Ugni blanc (tolerant), together with the stock-vine 41B (tolerant) as well as four of its transformants: one having inserted supernumerary copies of the genes encoding a stilbene synthetase (13 kb insert), i.e. clone 55-3, and the three others representing transformants harbouring the PMs PR10-1 promoter-vst1 gene construct, that is clones 145-2, 145-5 and 145-6.

b) Results Obtained

The results for the foliar symptoms observed at 2 or 5 days after the inoculation are presented in Tables 7 and 8 and the results for the assays of resveratrol, related either to dry weight or to chlorophyll content, are presented in Tables 9 and 10.

TABLE 7

Macroscopic observations of vitroplant
leaf/*Botrytis cinerea* interactions at 2 days

| Variety tested | Number of No. 4 leaves observed in 4 different plants in which the following symptoms appear | | |
|---|---|---|---|
| | Regions of maceration | Necrotic spots | No visible symptom |
| Folle blanche 280 | 4 | 1 | 0 |
| Pinot noir 386 | 3 | 4 | 0 |
| Ugni-blanc 479 | 1 | 2 | 1 |
| 41B | 0 | 4 | 0 |
| Pct 55-3 | 2 | 3 | 0 |
| Pct 145-2 | 0 | 3 | 1 |
| Pct 145-5 | 0 | 1 | 3 |
| Pct 145-6 | 1 | 1 | 2 |

Legend to Table 7:
  Regions of maceration: broad and diffuse region in which Botrytis is rapidly destroying the plant cells. These regions have a light brownish beige colour.
  Necrotic spots: very small regions centred around the fungus. These spots have a blackish brown colour.

TABLE 8

Macroscopic observations on the vitroplant
leaf/*Botrytis cinerea* interactions at 5 days

| Variety tested | Number of No. 3 leaves observed in 4 different plants in which the following symptoms appear | | |
|---|---|---|---|
| | Regions of maceration | Necrotic spots | No visible symptom |
| Folle blanche 280 | 4 | 0 | 4 |
| Pinot noir 386 | 3 | 1 | 2.5 |
| Ugni-blanc 479 | 2 | 1 | 0.5 |
| 41B | 1.5 | 2 | 0.5 |
| Pct 55-3 | 2 | 2 | 1 |
| Pct 145-2 | 1.5 | 2 | 1 |
| Pct 145-5 | 0.5 | 4 | 0 |
| Pct 145-6 | 3 | 2 | 1 |

Legend to Table 8:
  Regions of maceration: broad and diffuse region in which Botrytis is rapidly destroying the plant cells. These regions have a light brownish beige colour.
  Necrotic spots: very small regions centred around the fungus. These spots have a blackish brown colour.

TABLE 9

Results of the HPLC assays of resveratrol which
were carried out on different grapevine varieties which
had been interacting with *Botrytis cinerea* for 2 days

| Variety tested | Resverat. $mg \cdot g^{-1}$ of chloroph. | Resverat. $\mu g \cdot g^{-1}$ of dry weight |
|---|---|---|
| Folle B280 | 5.1 | 101 |
| Pinot N386 | 4.3 | 102 |
| Ugni B479 | 3.9 | 86 |
| Stock-g41B | 5.7 | 112 |
| Pct 55-3 | 4.6 | 118 |
| Pct 145-2 | 6.9 | 170 |
| Pct 145-5 | 2.2 | 83 |
| Pct 145-6 | 4.3 | 107 |

Legend to Table 9:
  Resverat.: resveratrol; chloroph.: chlorophyll Folle B 280: Folle blanche 280; Pinot N 386: Pinot noir 386; Ugni B 479: Ugni-blanc 479; Stock-g41 B: Stock-vine 41B

TABLE 10

Results of HPLC assays of resveratrol which
were carried out on different grapevine varieties which
had been interacting with *Botrytis cinerea* for 9 days

| Variety tested | Resveratrol $mg \cdot g^{-1}$ chlorophyll | Resveratrol $\mu g \cdot g^{-1}$ of dry weight |
|---|---|---|
| Folle blanche 280 | 4.0 | 38 |
| Ugni-blanc 479 | 31.7 | 145 |
| Stock-vine 41B | 11.9 | 59 |
| Pct 145-5 | 602.1 | 2558 |

→Two Days After Inoculation:

The observation related to the youngest leaves (row 4). Regions of maceration (colonization by the fungus) were observed in almost all cases, apart from 41B and clones 145-2 and 145-5. The susceptible grapevine varieties exhibited these regions to a greater extent than did the tolerant varieties: Folle blanche and Pinot noir exhibited 4 and 3 regions, respectively, as against only 1 in the case of the Ugni blanc variety. Only the 145 transformants (PMs PR10-1 promoter-vst1gene) and the Ugni blanc gave leaves without visible symptoms. Necrotic regions, which are a plant defence reaction, appeared mainly in 41B and its transformants and, in the case of the grapevine varieties, in Pinot Noir and Ugni blanc.

If these observations are compared with the resveratrol assays (Table 9), it is not possible to establish any correlation since, when related to dry weight, the contents of resveratrol in these leaves are comparable with a value of approximately 100 $\mu.g^{-1}$ of dry material. In all the vitroplants examined, the contents settle at values of between 4 and 5 $mg.g^{-1}$ of chlorophyll.

It is only the stock-vine 41B and, in particular, transformant 145-2 which have higher values. Clone 145-5 has a lower value (approximately half the size).

A comparison can also be made with the resveratrol contents which were previously obtained at 20 hours after inducing the vitroplants with UV light (Table 6). Although the period of sampling is not comparable (20 hours in the case of the abiotic stress as compared with 48 hours in the case of the biotic stress, although the time necessary for the germination of the spores has to be taken into account), lower contents of resveratrol are generally observed after a biotic stress (half or one third, in the case of the Ugni blanc, of the amount), apart from the Pinot noir, where the content is comparable, and the Folle blanche, where the content is approximately three times greater.

In all the samples analysed, it may be emphasized that there was a marked scattering of the values obtained in the different repeat assays which were performed. This variability between different leaves of one and the same plant, which was previously observed with the samples which had been subjected to the UV light inductions, could, in the latter case too, be due to several different factors. The most plausible hypotheses which may be mentioned are:

A wide variability between vitroplants of one and the same clone in their reaction in the face of fungal attack. The variable foliar symptoms which were obtained following inoculation with the Botrytis spores appear to confirm this (variability in the infection, in the physiological state of each plant, etc.).

The assay, which is performed on the whole leaf, is not representative of the variations in the synthesis of resveratrol which exist in each cell which forms the leaf. Thus, it is generally acknowledged that, in hypersensitivity reactions to a parasite, it is not all the cells of the lamina which synthesize defence molecules. It is only the cells which are located close to the regions of fungal attack which are induced to synthesize phytoalexins. Therefore, the analyses which were performed in this test only represent values which correspond to a mean resveratrol level which is present in the lamina of leaves which are interacting with the parasite. A sizeable dilution effect can therefore be produced, in particular in the case of the resistant plants, between the concentrations which are present in the cells which are induced to synthesize phytoalexin and the value which is found when the whole leaf is analysed. This effect is doubtless more marked during the early stages of expression of the plant defence reactions.

→Five days after the inoculation:

The symptom observations show (photographic plates Nos. 1 and 2) (FIGS. 10 and 11) and Table 8) that regions of maceration are formed, in relatively large numbers, in all the grapevine varieties, in the stock-vine and in the transformants which were studied. These maceration regions are often associated with the presence of conidiophores (fruiting bodies of the fungus). Of the grapevine varieties and the control stock-vine 41B, the Folle blanche, which is the species which is most susceptible to Botrytis, shows attacks on all the leaves studied, and also conidiophores. If a hierarchy in the severity of the symptoms is established, the Pinot noir comes next, followed by the Ugni blanc and finally 41B. However, in the case of these two latter varieties, conidiophores only developed on one single half-leaf. As far as the transformant clones are concerned, three clones gave reactions which were more or less similar: 55-3, 145-2 and 145-6. Only clone 145-5 exhibited good tolerance to the parasite since a region of maceration only developed on one half-leaf and no conidiophores were visible.

On the other hand, most of the leaves of this clone reacted to the attack by forming necrotic regions. An example is also depicted in photographic plate 2 (FIG. 11).

In order to verify whether these results corresponded satisfactorily to the marked differences in the induction of resveratrol synthesis, and therefore to the expression of gene(s) encoding a stilbene synthetase, leaves which were inoculated with the Botrytis spores were inspected by fluorescence microscopy (filter unit A: excitation filter of from 340 to 380 nm; stop filter at 425 nm). Under these conditions, chlorophyll fluoresces red while resveratrol fluoresces bluish white or a darker blue depending on its concentration. Two grapevine varieties, i.e. Folle blanche (susceptible) and Pinot noir (moderately tolerant), the stock-vine 41B (tolerant) and one of its transformants, i.e. 145-5 (PMs PR10-1 promoter- vst1 gene construct), were studied by this method. The photographs obtained from these observations are presented in photographic plate 3 (FIG. 12). Striking differences can be seen. In the case of the Folle blanche, the parasite mycelium (black in the photograph) has developed and has colonized the tissues. Practically no bluish cell is visible. In the case of the Pinot noir variety, a bluish region can be observed, which region forms a barrier around and in the region of inoculation and incipient colonization by the fungus. The growth of the mycelium is retarded, if not blocked, by this barrier, even if a tissue maceration process has already been instituted. A more intense blue coloration also exists in the veins. In the region studied in the case of the control stock-vine 41B, scattered cells, which are distributed throughout the lamina, display a light blue fluorescence with an intensity which is greater in the veins. No fungal colonization process has been instituted, and scattered necrotic regions, which are limited to a few cells, can be seen. With regard to the 41B which is transformed with the PMs PR10-1 promoter-vst1 gene construct, the results are spectacular in the case of clone 145-5. While incipient colonization of the tissues by the fungus has been instituted (black region), a cell barrier, which is synthesizing resveratrol, has formed very rapidly around this region thereby preventing it from being extended. Blue cells are still visible in the region of fungal maceration. Furthermore, many of the cells of the lamina of the leaf which are not in contact with the fungus have themselves synthesized resveratrol. The veins also display an intense blue coloration.

These observations demonstrate that a correlation therefore exists between the intensity of the foliar symptoms which developed after inoculating vitroplants with Botrytis spores and the content of stilbenic phytoalexin in the leaves. The most tolerant plants are those which display a resveratrol synthesis which is distributed over a large part of the lamina. This is the case with transformant 145-5, which harbours a gene encoding a stilbene synthetase under the control of the PMs PR10-1 promoter, which promoter was isolated from lucerne.

→Nine Days After Inoculation:

The symptom observations demonstrated that the Folle blanche vitroplants were particularly susceptible to Botrytis attacks in this test as well. At nine days, they are all infested with the fungus and their chlorophyll is markedly degraded in most cases. With regard to the Ugni-blanc variety and the stock-vine 41B, it was not possible to observe any difference in expression of the foliar symptoms. Generally speaking, the symptom observation results which were obtained at 5 days are encountered once again while being a little more developed in the case of the regions of maceration. On the other hand, most of the leaves which exhibited conidiophores have necrosed.

4 varieties were analysed for their content of resveratrol: the Folle blanche (susceptible), the Ugni-blanc (tolerant), the 41B (tolerant) and 145-5 (41B transformed with the PMs PR10-1 promoter-vst1 gene). Nine days after inoculation, 145-5 still did not exhibit any significant symptoms of Botrytis attack. The results of the resveratrol content analyses are presented in Table 10. When expressed in gg of resveratrol $.g^{-1}$ of dry weight or in $mg.g^{-1}$ of chlorophyll, the resveratrol concentrations can be used to rank the varieties in the following manner, proceeding from the lowest value to the highest: Folle blanche<41 B<Ugni-blanc<the transformed 41B strain 145-5.

The concentration differences are very substantial since the transformant 145-5 has a value which is almost 43 times greater than that of the 41B control (per g of dry weight) and 50 times greater if it is expressed per g of chlorophyll. The assays therefore provide good confirmation of the fluorescence microscopy assessments that were made at five days (see photograph plate 3, FIG. 12).

With regard to-the Ugni-blanc and the 41B, Table shows that the former has approximately 3 times more resveratrol than the latter whichever units are selected. However, these two varieties react in an identical manner in terms of foliar symptoms. This similarity in tolerance can be explained by factors other than the synthesis of resveratrol. It must also be noted that, under the conditions of the test, the plant/Botrytis confrontation is particularly favourable to the latter. The environmental conditions which exist in a container in vitro ensure that, after approximately days of culture, all the vitroplants, whatever their nature, are infected with the fungus.

c) Conclusions on the Genetic Transformation of Agrapevine and Analysis of the Efficiency of the Promoters Studied It was not possible to regenerate plants containing the constructs which comprised the vst1 gene under the control of the 35S promoter or its derivatives from the experiments on 41B (stock-vine hybrid *V. Vinifera×V. Berlandieri*) embryogenic cells which were transformed with *Agrobacterium tumefaciens* harbouring the different constructs. It was not therefore possible to obtain any strong constitutive activity over the whole of the plant.

By contrast, grapevine plants which had incorporated the PMs PR10-1-vst1 gene and 13 kb insert constructs (vst1 and vst2 genes under the control of their native promoters) were obtained. It was possible to compare these genetically transformed plants with the control (41B untransformed) and multiply them by micropropagation.

Few differences were observed, as compared with the untransformed controls, in the concentrations of resveratrol which were obtained, under UV light stress (biotic stress), in the different transformants which were prepared with the 13 kb insert, in which two genes, i.e. vst1 and vst2, both of which are under the control of their native promoters, are present in the sequence used as insert.

By contrast the results demonstrate that the chimeric PMsPR10-1-vst1 gene construct enables an approximately 50-fold overexpression of the phytoalexin resveratrol (product of reaction catalysed by a stilbene synthetase) to be achieved, in the presence of a biotic stress caused by Botrytis cinerea, at 9 days after infection. These plants then demonstrate the best tolerance when they are compared either with the control or with the transformants which were obtained with the 13 kb insert.

Thus, transformation with the construct which links the inducible lucerne promoter PMs PR10-1 to the stilbene synthetase genes enables the stilbene synthetase genes to be overexpressed in grapevine plants in response to a stress such as pathogen attack.

References

BEVAN M. 1984. Binary Agrobacterium vectors for plants transformation Nucl. Acids Res., 12, 8711–8721.

BLONDON F. 1964. Contribution à l'étude du développement des graminés fourragères: Ray gras et Dactyle. (Contribution to the study of the development of forage grasses: Rye grass and orchard grass). Rev. Gén. Bot., 71, 293–381.

CASSE-DELBART, F., 1996. La transgénèse Végétale. Les Plantes Transgéniques en Agriculture (Plant transgenesis. Transgenic plants in agriculture), John LIBREY Eurotext, ISBN: 27420-0149-2, 59–88.

DAÏ G. H. 1994. Etude des facteurs biochimiques de résistance de la vigne (Vitis spp) au mildiou (*Plasmora viticola*). Thèse de doctorat de l'Ecole Nationale Supèrieure Agronomique de Montpellier (France) (Study of the biochemical factors involved in the resistance of grapevine (Vitis spp) to mildew (*Plasmora viticola*). Doctoral thesis of the National College of Agriculture at Montpellier (France)).

DITTA G., SCHbMIDTHAUSER T., YACOBSON E., LU P., LIANG A. W. et al., 1985. Plasmid related to the broad range vector, pRK290, useful for gene cloning and for monitoring gene expression. Plasmid 13, 149–153.

ESNAULT R., BUFFARD D., BREDA C., SALLAUD C., EL TURK J., KO NDOROSI A., 1993. Pathological and molecular characterizations of alfafa interactions with compatible and incompatible bacteria *Xanthomonas campestris* pv. Alfalfae and *Pseudomonas syringae* pv. pisi. Mol. Plant-Microbe Interaction 6, 655–664.

FISHER R. and HAIN R.; 1994. Plant disease resistance resulting from the expression of foreign phytoalexins. Current Opinion in Biotechnology, 5, 125–130.

HAIN R., REIF H. J., KRAUSE E., LANGEBARTELS R., KINDL H., WORNAM B., WIESE W., SCHMELZER E., SCHREIER P. H., STOECKER R. H. and STENZEL K. 1993. Disease resistance results from foreign phytoalexin expression in a novel plant. NATURE, 361, 153–156.

LANGCAKE P. and PRYCE R. J., 1977. A new class of phytoalexins from grapevines. Experientia, 33, 151–152.

MELCHIOR F. and KINDL M., 1991. Coordinate and elicitor dependent expression of stilben synthetase and phenyl ammonia lyase genes in Vitis cv optima. Arch. Biochem. Biophys., 288, 2; 552–557.

MURASHIGE T. and SKOOG F. 1962. A revised medium for rapid growth and bioassay with tobacco tissue cultures. Physiol. Plant. 15, 473–497.

NEGRETIU, I. and GHARTI-CHHETRI, G. B., 1991. A Laboratory Guide for Cellular and Molecular Biology, BIOMETHODS; SALUZ H. P. and BECKER, M. M., Series Eds., BIRKHAUSER VERLAG, 105–122.

PETIT A., STOUGAARD J., KUHLE A., MARCKER K. A. and TEMPE J. 1987. Transformation and regeneration of the legume: *Lotus cornitulatus*. A system for molecular studies of symbiotic nitrogen fixation. Mol. Gen. Genet. 207, 245–250.

PIETRZAK M., SHILLITO R. D., HOHN T., and POTRYKUS I. 1986. Expression in plants of two bacterial antibiotic genes after protoplast transformation with a new plant expression vector; Nucl. Acids Res. 14 (14), 5857–5869.

PONT V. and PEZET R., 1990; Relation between the chemical structure and the biological activity of hydroxystilbenes against *Botrytis cinerea. J. Phytopath.*, 130, 1–8.

REAM, W., 1989. *Agrobacterium tumefaciens* and interkingdom genetic exchange. Ann. Rev. Phytophat., 27, 583–618.

SBAGHI M., 1993. Aspects physiologiques et biochimiques interaction Vigne-*Botrytis cinerea*. Thèse de doctorat l'Universit6 de Bourgogne (France) (Physiological and biochemical aspects of the grapevine/*Botrytis cinerea* interaction. Doctoral thesis of the University of Burgundy (France)).

STANFORD J. C., 1990. Biolistic plant transformation, Physiol. Plant. 79, 20614 209.

SZABADOS L., CHARRIER B., KONDOROSI A., De BUIJN F. T., and RATET P. 1995. New promoter and enhancer testing vectors. Molecular Breeding.

VANCANNEYT G., SCHMIDT R., O'C.ONNOR-SANCHEZ A., WILLMETZER L. and ROCHA-SOZA M. 1990. Construction of an intron-containing markergene: splicing of the intron in transgenic plants and its use in monitoring early evenys in Agrobacterium-mediated transformation. Mol. Gen. Genet. 220, 245–250.

VAN LOON L. C. 1985. Pathogenesis Related Proteins. Plant Mol. Biol. 4, 111–116.

VAN LOON L. C., PIERPOINT W. S., BOLLER T., CONEJERO V. 1994. Reconmmendations for naming plant pathogenesis related proteins. Plant Mol. Biol. Rep 12, 245–264.

WIESE W., VORNAM B., KRAUSE E. and KINDL H., 1994. Structural organization and differential expression of three stilbene genes located on a 13 kb grapevine DNA fragment. Plant Mol. Biol., 26, 2, 667–677.

What is claimed is:

1. An isolated nucleic acid molecule which comprises a promoter for a gene encoding a lucerne pathogenesis-related protein operably linked to a DNA encoding stilbene synthase, wherein said nucleic acid molecule comprises SEQ ID NO: 3.

2. A plant expression vector comprissing the nucleic acid of claim 1.

3. The plant expression vector according to claim 2, wherein said vector is a plasmid.

4. The plant expression vector according to claim 2, wherein said vector can be transferred into Agrobacterium.

5. A plant cell transformed with the plant expression vector of claim 2.

6. The plant cell according to claim 5 wherein said cell is a grapevine cell.

7. A method for making a plant cell that expresses stilbene synthase comprising:

transforming a plant cell with an expression vector compromising SEQ ID NO: 1 operably linked to SEQ ID NO: 2.

8. A method for making a plant that express stilbene synthase comprising:

transforming a plant cell with the plant expression vector of claim 2; and regenerating a transformed plant from said cell.

9. A tansformed plant comprising the plant expression vector of claim 2.

10. A transformed plant made by the method of claim 8.

11. An isolated nucleic acid molecule comprising SEQ. ID. NO.: 1.

12. An isolated nucleic acid molecule comprising SEQ. ID. NO.: 2.

* * * * *